（12） United States Patent
Perscheid

(10) Patent No.: US 10,952,649 B2
(45) Date of Patent: Mar. 23, 2021

(54) HEARING ASSIST DEVICE FITTING METHOD AND SOFTWARE

(71) Applicant: IntriCon Corporation, Arden Hills, MN (US)

(72) Inventor: Andreas Perscheid, Ruedesheim (DE)

(73) Assignee: Intricon Corporation, Arden Hills, MN (US)

( * ) Notice: Subject to any disclaimer, the term of this patent is extended or adjusted under 35 U.S.C. 154(b) by 0 days.

(21) Appl. No.: 16/601,368

(22) Filed: Oct. 14, 2019

(65) Prior Publication Data
US 2020/0069224 A1 Mar. 5, 2020

Related U.S. Application Data

(63) Continuation-in-part of application No. 15/846,521, filed on Dec. 19, 2017.

(60) Provisional application No. 62/745,085, filed on Oct. 12, 2018, provisional application No. 62/573,549, filed on Oct. 17, 2017, provisional application No. 62/466,045, filed on Mar. 2, 2017, provisional application No. 62/436,359, filed on Dec. 19, 2016.

(51) Int. Cl.
*A61B 5/12* (2006.01)
*G06F 3/0484* (2013.01)
*H04R 25/00* (2006.01)
*A61B 5/00* (2006.01)
*G16H 20/00* (2018.01)
*A61N 1/36* (2006.01)

(52) U.S. Cl.
CPC ............ *A61B 5/123* (2013.01); *A61B 5/4836* (2013.01); *A61B 5/7435* (2013.01); *A61B 5/7475* (2013.01); *G06F 3/04847* (2013.01); *G16H 20/00* (2018.01); *H04R 25/70* (2013.01); *A61N 1/36039* (2017.08)

(58) Field of Classification Search
CPC ..... A61B 5/123; A61B 5/4836; A61B 5/7435; A61B 5/7475; G16H 20/00; G06F 3/04847; H04R 25/70; A61N 1/36039
USPC .......................................................... 381/60
See application file for complete search history.

(56) References Cited

U.S. PATENT DOCUMENTS

| 6,447,461 | B1 | 9/2002 | Eldon |
| 6,840,908 | B2 | 1/2005 | Edwards et al. |
| 7,024,000 | B1 | 4/2006 | Gabara et al. |
| 7,599,499 | B2 | 10/2009 | Naylor |
| 8,112,166 | B2 | 2/2012 | Pavlovic et al. |
| 8,135,138 | B2 | 3/2012 | Wessel et al. |
| 9,131,321 | B2 | 9/2015 | Sabin |
| 9,319,812 | B2 | 4/2016 | Banerjee et al. |

(Continued)

*Primary Examiner* — Sean H Nguyen
(74) *Attorney, Agent, or Firm* — Jeffrey D. Shewchuk; Shewchuk IP Services, LLC

(57) ABSTRACT

A method and software program is used by patients for fitting and refitting of a DSP-based hearing assistance device. An audiologist user interface and patient user interface include soundmaps and slidebars to control collections of hearing parameters within the DSP of the device. Based on cognitive testing and training of the patient, the range of adjustment allowed within at least the patient user interface is limited. The software therefore always maintains 100% safety for the patient and/or user to finetune the hearing aid parameters without worrying about selecting parameter values which would leading to slowing the cognitive learning of the patient.

19 Claims, 22 Drawing Sheets

(56) References Cited

U.S. PATENT DOCUMENTS

| | | |
|---|---|---|
| 9,414,173 B1 | 8/2016 | Hou |
| 9,420,389 B2 | 8/2016 | Pontoppidan |
| 9,439,008 B2 | 9/2016 | Shennib |
| 9,445,754 B2 | 9/2016 | Schmitt |
| 9,468,401 B2 | 10/2016 | Van Hasselt et al. |
| 9,491,556 B2 | 11/2016 | Fitz et al. |
| 9,532,152 B2 | 12/2016 | Shennib |
| 9,699,576 B2 | 7/2017 | Wessel et al. |
| 9,782,131 B2 | 10/2017 | Van Hasselt et al. |
| 9,801,570 B2 | 10/2017 | Polley et al. |
| 9,946,842 B1 | 4/2018 | Stringham et al. |
| 10,185,834 B2 | 1/2019 | Adam et al. |
| 10,348,695 B1 | 7/2019 | Khassanov et al. |
| 10,424,031 B2 | 9/2019 | Neff |
| 2004/0071304 A1* | 4/2004 | Yanz ............... H04R 25/70 381/312 |
| 2010/0196861 A1 | 8/2010 | Lunner |
| 2014/0355798 A1* | 12/2014 | Sabin ............... H04R 25/70 381/314 |
| 2015/0003650 A1* | 1/2015 | Drexler ............ H04R 25/75 381/312 |
| 2016/0166181 A1 | 6/2016 | Shennib |
| 2018/0098720 A1* | 4/2018 | Raz ............... H04R 1/1091 |

\* cited by examiner

FIG. 15

Telekom.de

Your Auditory Training   Speech Differentiation Exercise

Profile 60   62 R/L   Points 388 — 96   122

You will hear a background noise on one or both sides. You will listen to a text which will start silent and become louder. If you recognize what the text is about please press the related picture.

There are 5 rounds.

Back — 48   Next — 34   24

HEARING ASSIST DEVICE FITTING METHOD AND SOFTWARE

CROSS-REFERENCE TO RELATED APPLICATION(S)

The present application is a continuation-in-part of U.S. patent application Ser. No. 15/846,521, filed Dec. 19, 2017, which claims the benefit of U.S. provisional patent application Ser. No. 62/436,359, filed Dec. 19, 2016, also claims the benefit of U.S. provisional patent application Ser. No. 62/466,045, filed Mar. 2, 2017, and also claims the benefit of U.S. provisional patent application Ser. No. 62/573,549, filed Oct. 17, 2017. The present application also claims the benefit of U.S. provisional patent application Ser. No. 62/745,085, filed Oct. 12, 2018. The contents of U.S. provisional patent application Ser. Nos. 62/436,359, 62/466,045, 62/573,549, and 62/745,085 are hereby incorporated by reference in entirety.

BACKGROUND OF THE INVENTION

Human hearing is generally considered to be in the range of 20 Hz to 20 kHz, with greatest sensitivity to sounds including speech in the range of 1 kHz to 4 kHz. Most people naturally learn at a young age to differentiate and distinguish between different sounds, particularly sounds used frequently in the particular language commonly spoken around that young person. As people age, often their hearing slowly deteriorates, often with high frequency hearing or hearing of particular sounds decreasing more significantly than low frequency or other particular sounds. Hearing aids, personal sound amplifier products ("PSAPs") and similar hearing assist devices are used by many people to increase/adjust the amplitudes (and perhaps frequency) of certain tones and sounds so they will be better heard in accordance with their hearing loss profile. Cochlear implants, which output an electrical pulse signal directly to the cochlea rather than a sound wave signal sensed by the eardrum, are another type of hearing assist device which may involve customizing the signal for an individual's hearing loss or signal recognition profile.

For many years, the consensus approach used by hearing aid manufacturers and audiologists has been to focus on seeking perfect sound-quality that adjusts the gain and output to the individual hearing loss of their patients. Audiologists commonly perform a "fitting" procedure for hearing assist devices, and patients usually visit a hearing aid shop/audiologist to get the initial examination and fitting. The hearing aid shop/audiologist takes individual measurements of their patients, often measuring the hearing loss profile of the person being fitted, and taking additional measurements like pure tone audiometry, uncomfortable loudness of puretones, and speech audiometry. Using proprietary or standard algorithms, the audiologist then attempts to adjust the hearing aid profile of various parameters in the hearing assist device, usually within a digital signal processor ("DSP") amplifier of the hearing assist device. For instance, primary parameters which are adjusted in fitting a particular DSP amplifier (an OVERTUS amplifier marketed by IntriCon Corporation of Arden Hills, Minn.) include overall pre-amplifier gain, compression ratios, thresholds and output compression limiter (MPO) settings for each of eight channels, time constants, noise reduction, matrix gain, equalization filter band gain settings for each of twelve different frequency bands, and adaptive feedback canceller on/off. The typical fitting process usually involves identifying the softest sound which can be heard by the patient at a number of different frequencies, optionally together with the loudest sound which can be comfortably heard by the patient at each of those frequencies.

With all of these various parameter settings which can be adjusted by the audiologist during fitting, there are millions of different audio signal transfer functions which can be achieved with any particular DSP-based hearing aid. If the hearing impaired person has no measurable hearing in some frequencies, the audiologist commonly minimizes or eliminates those frequencies in the output so as to provide the greatest signal to noise ratio (i.e., to provide the most information) in the frequencies that the hearing impaired person has measureable hearing. That is, the consensus approach is to eliminate sounds output in so called "dead regions", and thereby eliminate background noise that could detract from intelligibility. In addition, hearing aid manufacturers and/or audiologists use several features (like automatic reduction of low frequency gain, etc.) to keep the acceptance level of users high. While audiologists can be provided guidelines and default settings that make fitting easier, audiologist fitting of the hearing aid and selecting each of these different parameter values tends to be more of an art than a science.

More recently, hearing aid manufacturers have added the capability of hearing aids to use wireless accessories such as external microphones and connections to smartphones to increase the usability of their hearing aids in different listening situations. These new capabilities still retain the focus on providing an objective "best" quality sound and signal to noise ratio, assuming that the entire hard-of-hearing problem is in the degradation of the ear to convert sound into a single "best" signal fed to the user's brain.

Even with the plethora of advances in modern hearing assist devices, many users find even high quality hearing aids to be unacceptable in improving their hearing sufficiently back to their memory of better hearing and understandability of speech and other sounds in differing listening environments. Many users are unsatisfied with the performance of their hearing assist devices, either as not optimally fitted, or as the hearing assist device is used in different environments with sound profiles and voices which differ from those used by the audiologist during fitting, or as the device gets dirty or device performance otherwise degrades during use. Particularly for users having a hearing loss in the range of 30-50 decibels in the critical speech containing frequencies, current fitting methods, even with a high quality hearing aid and professional assistance, do not allow the user to sufficiently understand speech, particularly in a noisy environment, to the same degree they could at a younger age. Better fitting methods are needed.

SUMMARY OF THE INVENTION

The present invention is directed at a method and software program (including a graphical user interface) for upgraded fitting and refitting of a DSP-based hearing assistance device. Various parameters are provided, controllable such as with slidebars on audiologist fitting software, each of which controls a plurality of different DSP parameter settings in the hearing aid. A soundmap is then included, which allows simultaneous control over a plurality of the slidebars. At least the patient fitting user interface, and optionally also the audiologist's fitting user interface, is limited in accordance with the cognitive-hearing abilities of the patient.

BRIEF DESCRIPTION OF THE DRAWINGS

FIGS. 15-18 are screen shots used in a fourth preferred type of cognitive training/testing.

Figure 1:
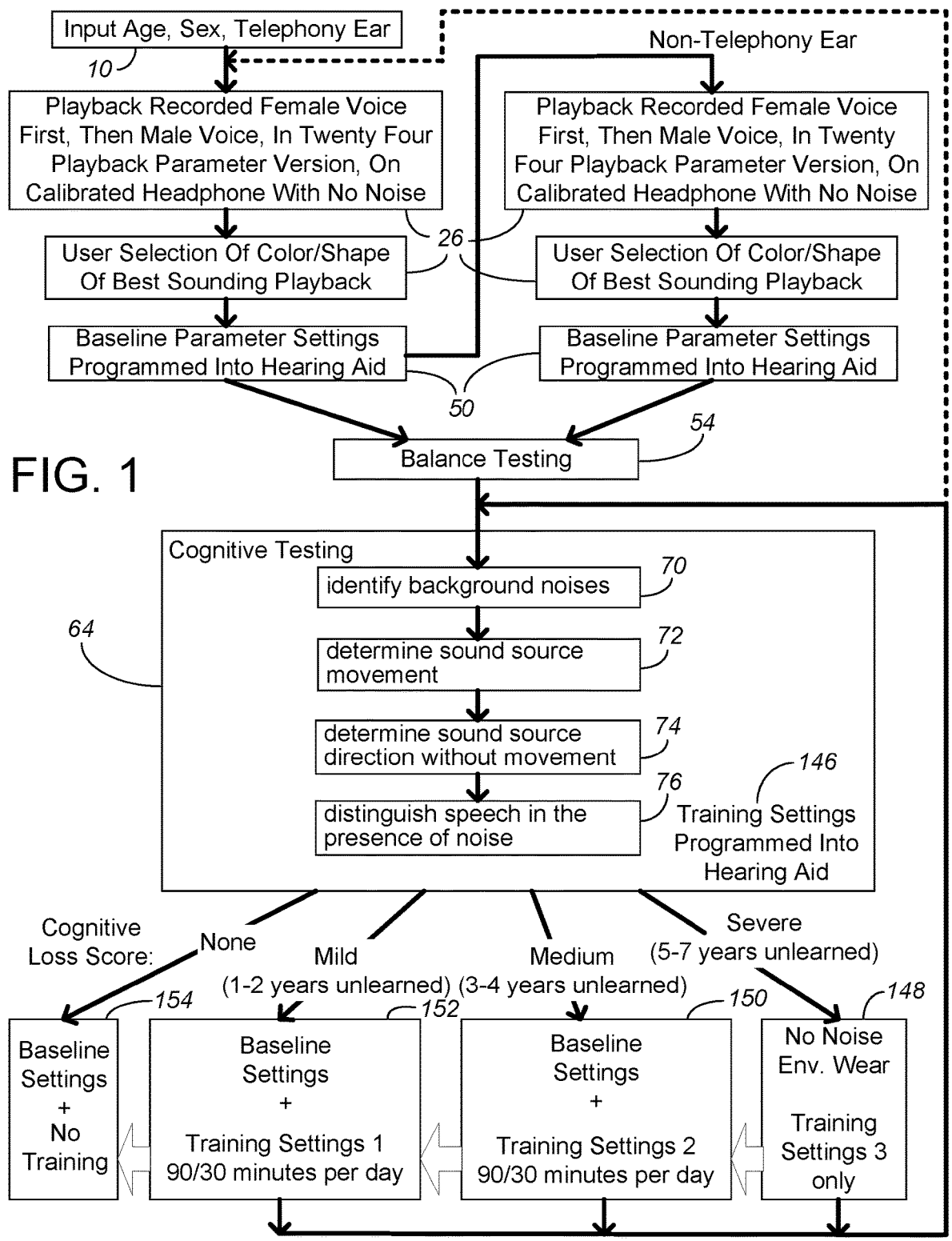
FIG. 1 is a flow chart of the preferred method of some aspects of the present invention.

While the above-identified drawing figures set forth preferred embodiments, other embodiments of the present invention are also contemplated, some of which are noted in the discussion. In all cases, this disclosure presents the illustrated embodiments of the present invention by way of representation and not limitation. Numerous other minor modifications and embodiments can be devised by those skilled in the art which fall within the scope and spirit of the principles of this invention.

DETAILED DESCRIPTION OF THE PREFERRED EMBODIMENT(S)

The present invention involves approaching the problem in the opposite direction from the established norm, focusing first on how sounds are subjectively interpreted in that particular user's brain. Only after measuring and considering that particularly user's subjective in-the-brain interpretation capability is the hearing assist device programmed, not to produce sound-quality that is objectively best, but rather to produce sound-quality which is best fit for that particular user's current sound-cognition abilities. In other words, the present invention first considers the brain and thereafter considers the ear, not like the consensus approach of considering the ear and ignoring deficiencies in the brain.

When interpreting sounds that are heard, the patient's brain compares the incoming signal with learned and remembered hearing patterns. For instance, consider an everyday situation in which there are multiple sound sources, such as having a conversation on a street corner, with both vehicles and other people passing by. All the sounds—from the vehicles, from the person in the conversation, from the other people passing by—are physically combined into a single sum sound signal heard by the ears. The brain attempts to separate the single sum signal into different identified and understood components. In making this separation, the heard audio signal is considered in the brain together with other data and situation patterns, like visual information, feelings, smells, etc. If, both based on sound cues such as critical bands and levels and based on the cues from the other senses, some portion of the incoming pattern is matched in the brain to correspond with a remembered pattern, the brain recognizes the incoming sound from an acoustic point of view. When matching incoming patterns to remembered patterns, the brain also has a tremendous ability to focus on selected portions of the incoming sound signal (what is being said by the other person in the conversation) while ignoring other portions of the incoming sound signal (the passing vehicles and noise from other people passing by).

A key feature of the way the brain identifies sound is that, when matching incoming/heard signals with remembered patterns, the brain also adjusts/reorganizes the remembered, existing patterns inside the brain to have a quicker and easier understanding next time, when confronted with a similar acoustic situation. For most people, the cognitive ability and learned/remembered sound patterns are established quite early, within the first few years of life. During most of a person's life (i.e., during the decades before identifying a hearing loss), the person is simply retreading through cognitive links that were established and known for as long as the person can remember.

As a person becomes hard-of-hearing, the incoming/heard signal changes. Information, that was present in the incoming signal at an earlier age, is no longer being received. The patient's cognitive linking by necessity also changes, i.e., what the user's brain remembers as an incoming audio pattern corresponding to speech is now different than the audio pattern heard/remembered years ago. Essentially, the patient forgets the "when I was younger, a recognized pattern sounded like this" cognitive link, replacing it with the more recent cognitive link of what a recognized pattern sounds like.

The problem with the consensus approach to hearing aids is that cognitive links in the patient's brain do not instantaneously return to their years-earlier state just because there is significantly more and better information in the incoming sound signal. The patient's brain does not instantly recognize newly received sound patterns that have not been heard (in that patient's brain) for years or decades. Even though a new hearing aid objectively provides near perfect sound to compensate for the hearing loss of the patient, the patient does not have cognitive links built for the new-hearing-sound-pattern. Speech can still be unintelligible because it does not match the cognitive links in that patient's brain as reconfigured over the recent years of being hard-of-hearing.

The present invention takes a very different approach. With the present invention, the hearing aid patient is hearing more sound like a baby, forming new cognitive links within the brain. The present invention focuses on trying to match the incoming sound signal with the patient's CURRENT cognitive links, not matching the incoming sound signal with cognitive links that were long ago forgotten. The present invention also focuses on trying to improve the brain's ability to recognize and match incoming sounds to existing/remembered patterns, i.e., a little by little improvement of the cognitive links in the user's brain toward maximum intelligibility, even if different from the cognitive links in place in the user's brain when the user had perfect hearing.

The method of the present invention can be utilized with a wide variety of hearing assist devices, including hearing aids, personal sound amplifiers, cochlear implants, etc. Use of the term "hearing aid" in this disclosure and figures is often merely for convenience in describing the preferred method, system, algorithm, software, performance testing and/or training, and should not be taken as limiting the invention to use only on hearing aids.

Figure 2:
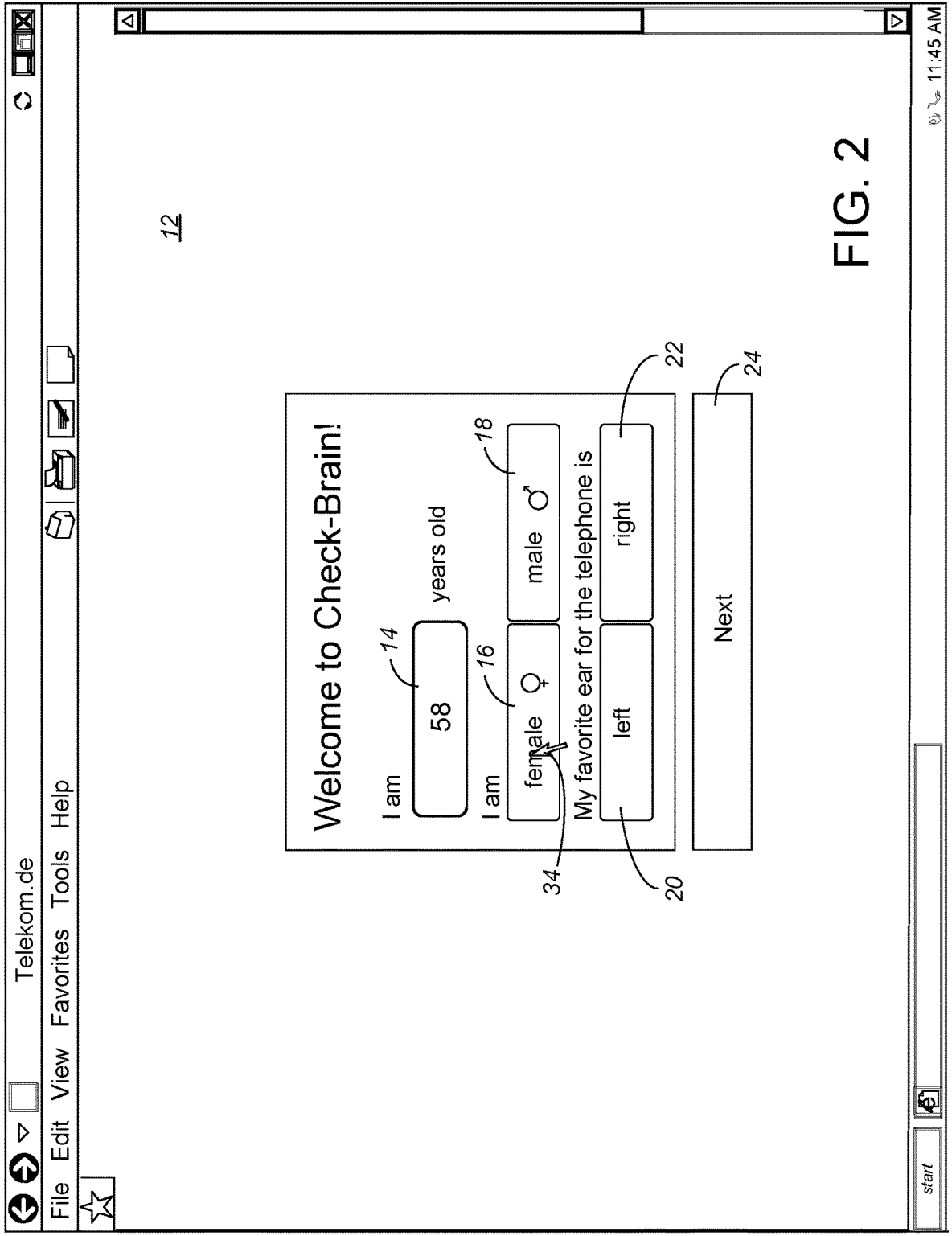
FIGS. 2-7 are screen shots of a preferred software program used to perform the hearing tests of the preferred method of FIG. 1.

As shown in the flowchart of FIG. 1, a first step 10 for the present invention is to input certain information about the patient which is separate from hearing and cognitive abilities. For instance, FIG. 2 shows an introductory question screen 12 of the preferred software. While FIG. 2 shows an example of a computer screen, the present invention is equally applicable for use on a more mobile device like a smartphone, a tablet or any other kind of mobile computing device having an audio output and a screen. The software can be provided either as a separate program which is downloadable or otherwise loaded on the computing device, or can reside on a server which is electronically accessible such as over the internet. Importantly, the software application and the depicted screen shots can be used anywhere, without being in a special measurement room inside a doctor's practice or in an audiologist's shop. The user fills in the user's age in a dialog box 14 (which could, if desired, include a drop down menu to select the user's age), has two buttons 16, 18 to click to identify gender, and has two buttons 20, 22 to click to identify preferred telephony ear. As explained below, the age, gender and telephony ear information are used as inputs into algorithms that determine the various parameters which can be set in the hearing aid DSP. Additionally, in the preferred embodiment, the sounds and questioning profile used in the remainder of the testing is dependent upon the age and gender responses the user inputs on this introductory question screen 12.

Patient age is an initial input in the system because the causes of hearing loss in younger patients tend to be different than in older patients, and thus the type of hearing loss in younger patients tends to be different than the type of hearing loss in older patients. As just one example, cerebrovascular and peripheral arterial disease have been associated with audiogram pattens and have been particularly associated with low frequency hearing loss. Accordingly, the patient's age can be used to provide DSP fitting settings that tend to be more appropriate for that particular patient.

Patient gender is an initial input in the system because male and female brains process sound differently. Studies indicate that females typically process voice sounds in Wernicke's area in the left cerebral hemisphere. Males tend to process male voice sounds in Wernicke's area, but process female voice sounds in the auditory portion of the right hemisphere also used for processing melody lines. Females tend to listen with both brain hemispheres and pick up more nuances of tonality in voice sounds and in other sounds (e.g., crying, moaning). Males tend to listen primarily with one brain hemisphere (either the left or the right, depending upon the sounds being heard and the processing being done in the brain) and do not hear the same nuances of tonality (e.g., may miss the warning tone in a female voice). Females also tend to be distracted by lower noise levels than males find distracting. These differences in sound processing also result in different exhaustion profiles of the brain. After long listening/processing sessions (such as typically in the evening), female brains tend to be exhausted overall on both hemispheres, while male brains are only exhausted on one side.

The present invention considers and adapts for these differences of typical brain processing of sounds by the different genders. For the hearing profiles of the present invention, women are provided with less overall gain, less loudness and more noise reduction to better understand speech, whereas men are provided with more gain between 1-4 kHz, thereby causing males to use the opposing side of the brain more like the exhausted side. These gender-based differences of DSP parameters settings are particularly appropriate for stressed situations of hearing and subsequent sound therapy, discussed further with reference to the training aspects of the present invention.

The ear that is favored for use on talking on the phone (so called "leading ear") is another initial input in the system, explained as follows. When speaking on the phone, the audio signal is only received in one ear. Because talking on the phone commonly involves using logic and analysis, most people migrate toward a preferred ear on the telephone which feeds the brain hemisphere better suited and/or trained for logic and analysis.

The present invention seeks to use these brain differences—one brain hemisphere better suited and/or trained for logic and analysis and the other brain hemisphere better suited and/or trained for creativity—to its benefit. For many users, the motivation to use a hearing assist device is to better understand speech. To separate speech from noise inside the brain, we would like the speech content best amplified with the least noise in the leading ear, with the percentage of noise being greater in the non-leading ear side. The non-leading ear is taking all the noise to separate it from speech inside the brain, i.e., to assist the patient's brain in identifying and ignoring the noise which is heard. The present invention thus inputs directional mirophone settings and higher noise reduction parameters into the hearing assist device worn in the leading ear, while inputting no microphone directionality and lesser noise reduction parameters parameters into the non-leading ear hearing assist device.

After (and preferably based on) the age, gender and telephony ear inputs, the user can click on a "Next" button 24 and the system proceeds 26 to testing of the hearing ability of each ear. Instead of performing pure tone audiometry, the preferred embodiment performs a relatively simple form of testing based on understandability of speech based on different playback parameters. Thus, the computing device used in performing the inventive method needs to have sound playback capabilities, preferably a electrical audio jack output which can be transformed into sound on carefully calibrated headphones.

FIGS. 3-7 represent the simplified hearing profile system testing aspect of the present invention. For each ear, the user merely plays through example recordings (shown here as a female voice 28 and a male voice 30), and controls the slider 32 to whichever of twenty-four locations permit the best hearing comprehension. The slide control can preferably be operated by a mouse 34, either by clicking on the arrows 36 or by click-drag-dropping the slider 32, or by arrows on the computer keyboard (if present, not shown). The preferred software includes a different playback curve for each slider position. In the preferred embodiment, the female/male voice playback differs for each of eight colors in amounts of general level of amplification and in each of three shapes in the shape of the gain-frequency curve (for instance, circle settings amplify the voice playback more in the low frequency registers, while triangle settings amplify the voice playback more in higher frequency registers, with square settings between the two). The female/male voice playback also differs for each of the eight colors and in each of the three shapes in compression and expansion characteristics. The specific control used to switch between voice playback characteristics is a matter of design choice.

Figure 3:
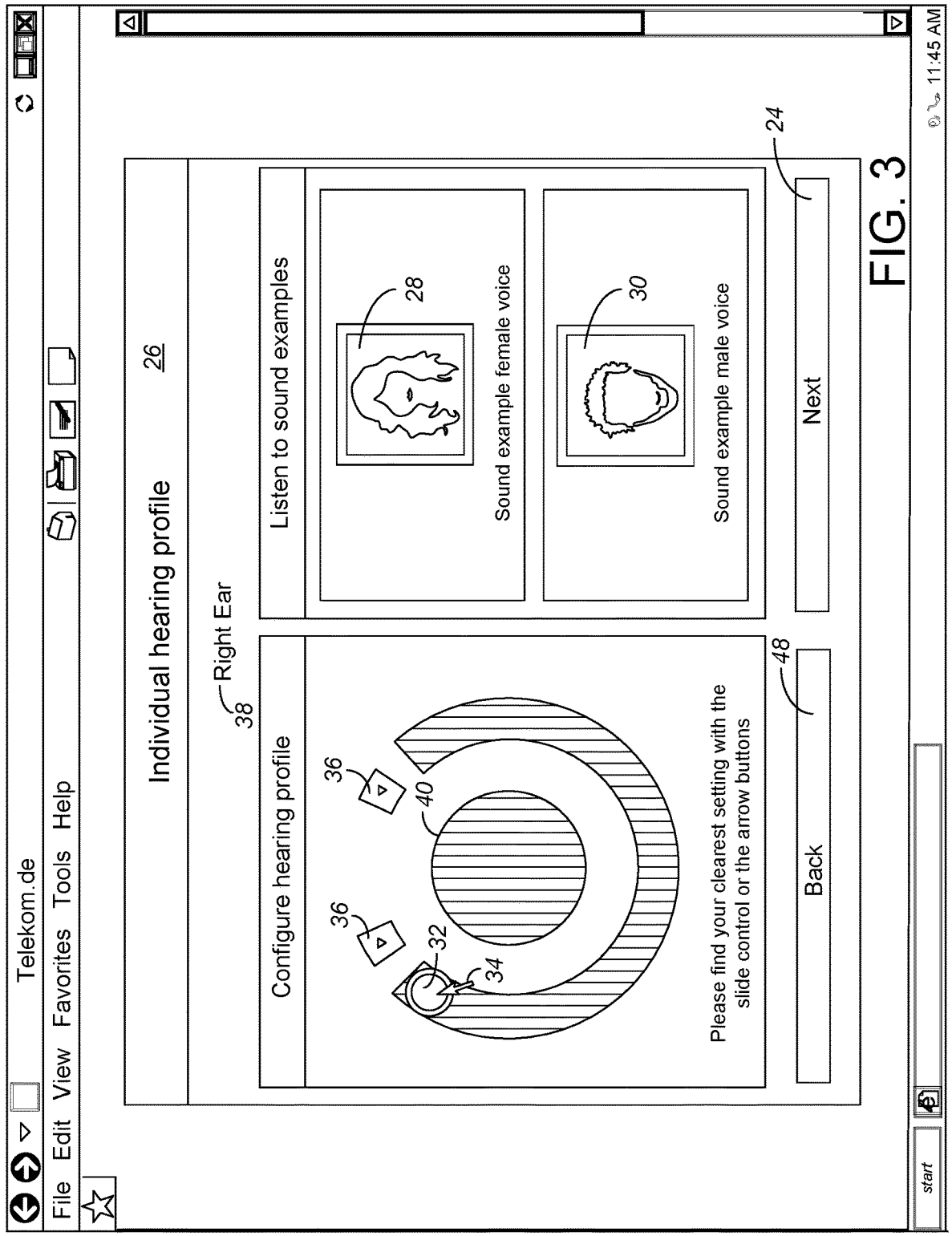
Figure 4:
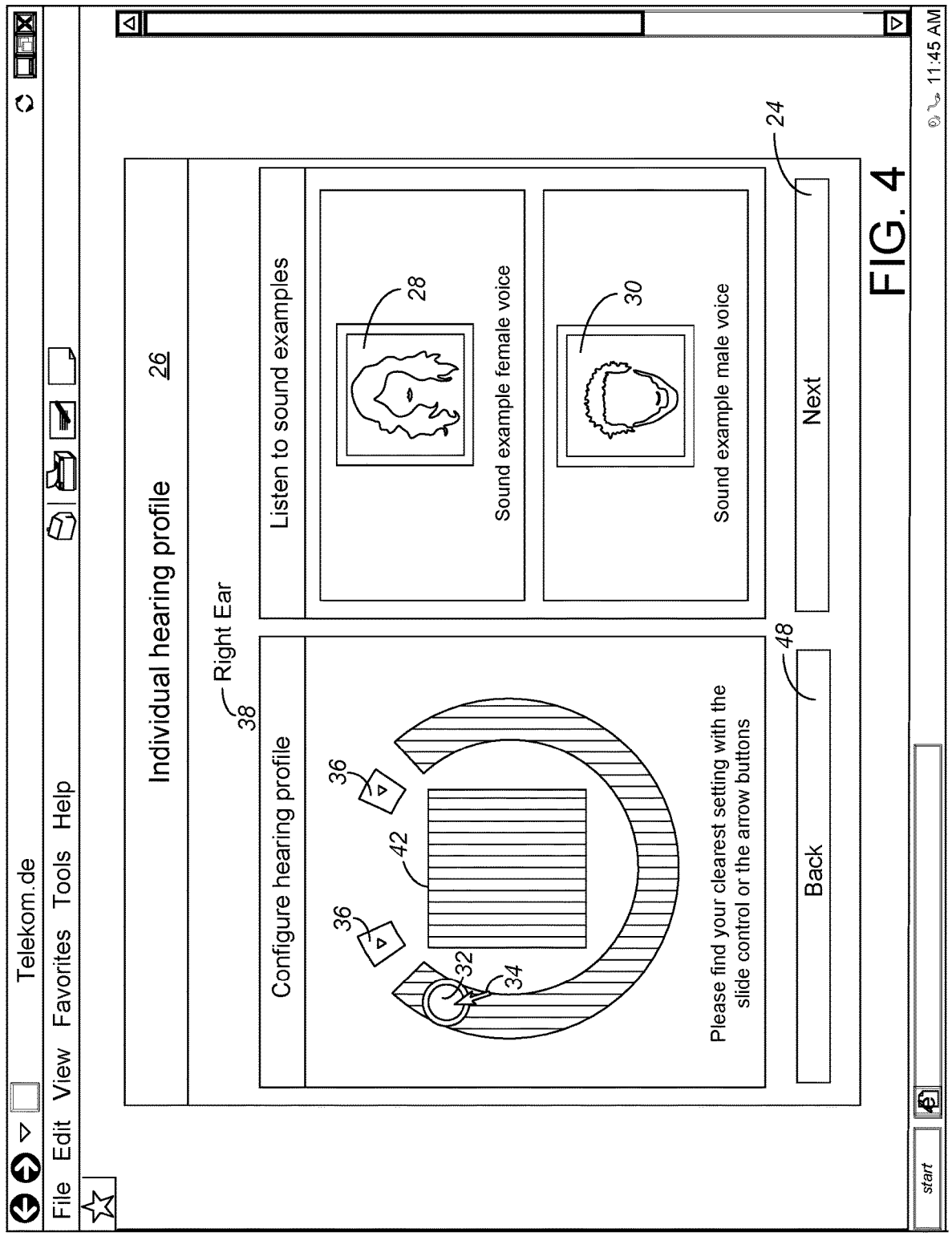
Figure 5:
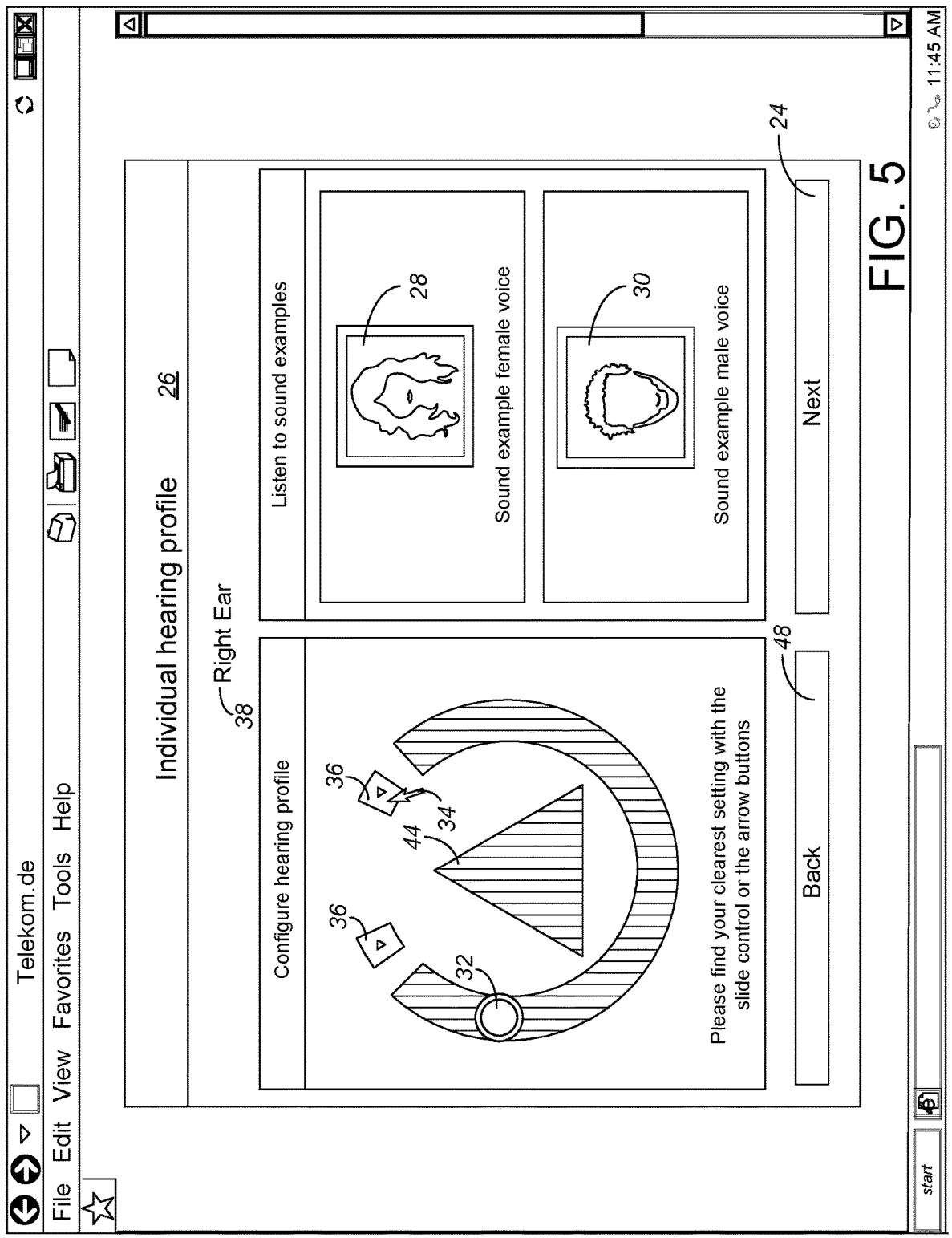
Figure 6:
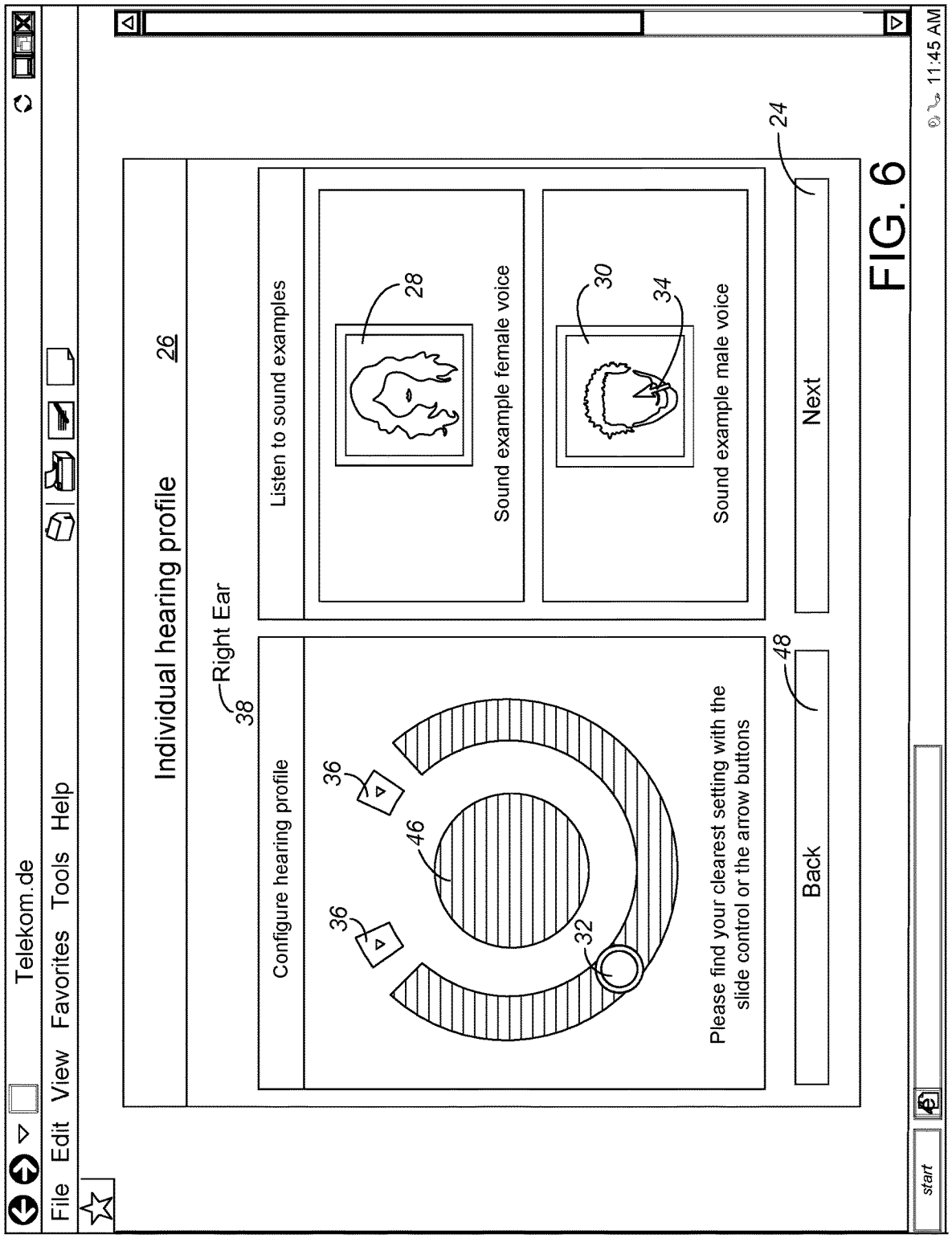

The objective is NOT to identify the minimum loudness of tones which can be heard or maximum volume which is comfortable for the patient's ears, but rather to identify which of the twenty-four different playback curves represents the characteristics of most easily understood speech for the hearing loss of that particular patient. The voice playback is preferably output on the calibrated headphones (not shown) into the ear of interest with essentially no noise. The test usually begins with the female voice 28, having a higher frequency profile than the male voice 30 and thus for most patients being harder to distinguish, and using the preferred telephony ear, which tends to be the dominant ear in cognitively understanding speech. So, for example and assuming the user has input that the right ear 38 is the preferred telephony ear, FIG. 3 shows a first slider position (the "red circle" selection 40) for the right ear 38. FIGS. 4, 5 and 6 show second ("red square" 42, arrived at by a click-drag-drop of the slider 32), third ("red triangle" 44, arrived at by clicking on one of the arrows 36) and seventh ("dark blue circle" 46) slider selection positions for the playback into the right ear 38. Each slider position changes the playback characteristics of the female voice 28. As the user clicks/drags the slider 32 to a different position, the color/shape 40/42/44/46 changes on the screen 26. If the user clicks on the male playback button 30 shown by the mouse 34 position in FIG. 6, the voice being played over the headphones changes to a male voice, again presented in twenty-four playback curves depending on slider position. The male voice 30, for which comprehension is generally as good as or better than the female voice 28, is preferably used to confirm the playback selection made with the female voice 28. The user can click back and forth between the male playback button 30 and the female playback button 28, in between adjusting the slider position, with the objective of selecting which of the twenty-four playback curves leads to the best intelligibility for both male and female speech.

For ease of distinguishing, the twenty-four possible slider positions for each ear 38 are separated into eight colors (red, orange, dark blue, green, light blue, purple, yellow, violet) by three shapes (circle, square, triangle). While the number of selectable slider positions could have been chosen to be about as low as six per ear to as high as hundreds of potential positions, other embodiments preferably include from ten to thirty slider positions per ear, with the preferred number of slider positions being twenty-four for each ear (only one left ear and four right ear slider positions depicted).

Figure 7:
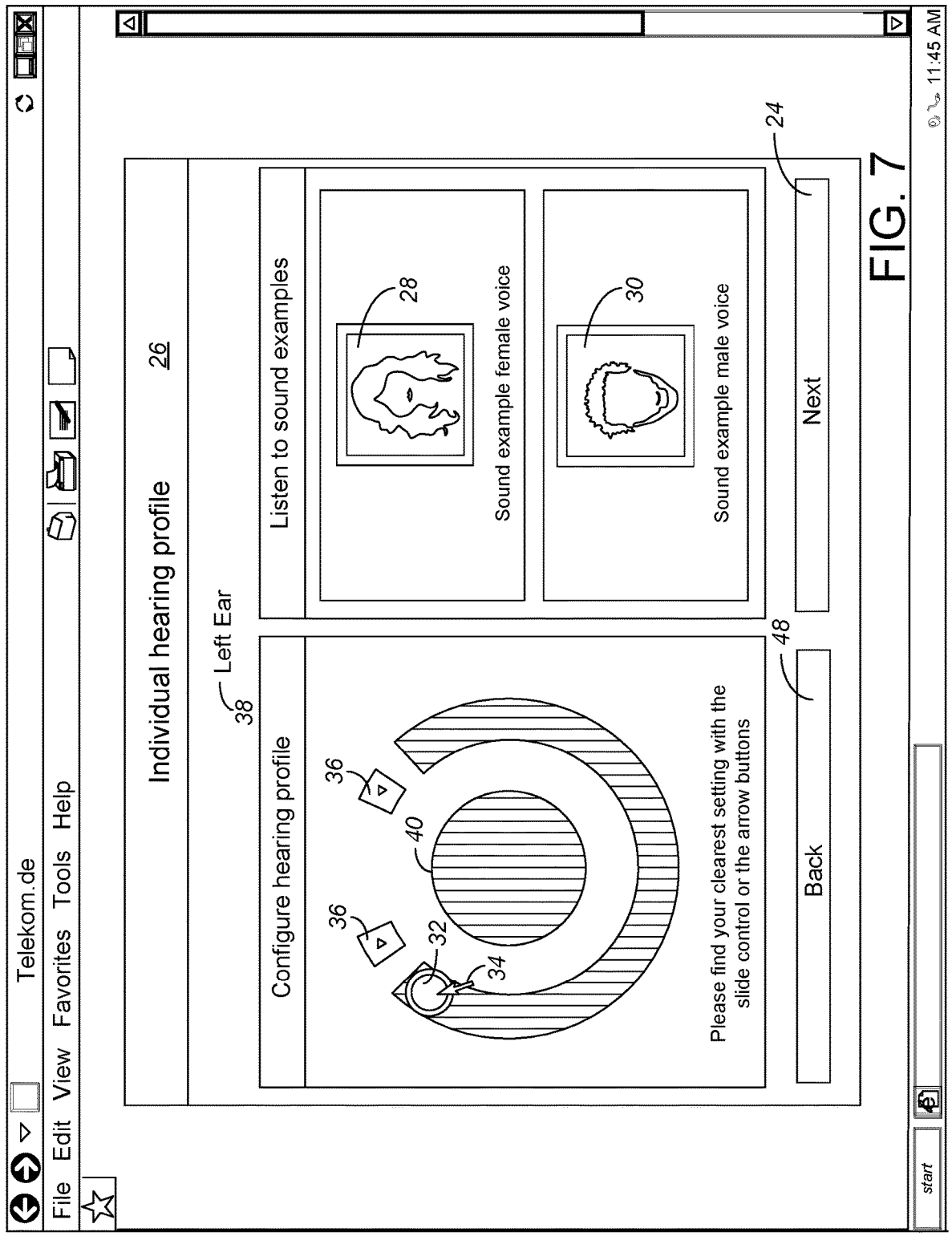

After selecting the color/shape for the preferred telephony ear, the user can click the "Next" button 24, and the testing is performed for the non-leading ear. FIG. 7 shows a first slider position (the "red circle" selection 40) for the left ear 38, recognizing that all twenty-four slider positions are again available, for both the male and female voice playback. A "Back" button 48 is provided if the user wishes to change settings or data which has been entered on previous screens.

In basic terms, based on testing of numerous hearing impaired individuals, the inventors have determined, and incorporated into the playback software, characteristics of male and female speech which can be best understood, in twenty four versions, by the vast majority of hearing impaired individuals. These sets of curves of playback settings are then plugged through for selection by the user while taking the test. The right and left hearing selections that the user can personally set in the field (i.e. outside the audiologists office) are then used, preferably together with the age, gender and telephony ear inputs, as inputs as variables into algorithms that convert between the input data and the various parameters which can be set in the DSP 50 to improve intelligibility.

Figure 8:
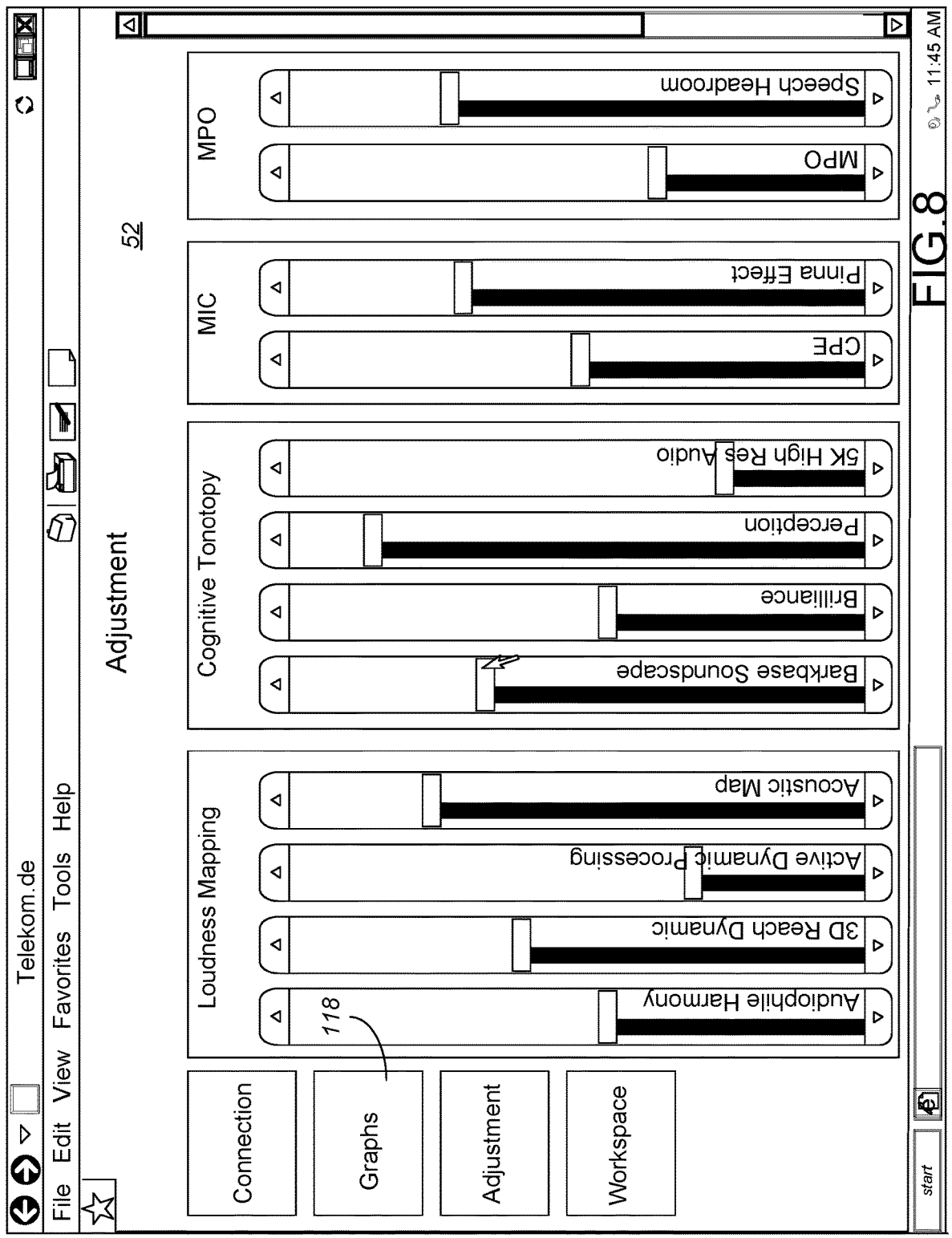
FIG. 8 is a screen shot of a first embodiment of an adjustment screen which can be used in the method of FIG. 1.

If desired, additional audio control and adjustment screens can be provided, more traditionally akin to those familiar to audiologist professionals, to set additional parameters in the DSP which are not modified in the basic algorithm, and/or to tweak the settings obtained through the simple hearing intelligibility test of FIGS. 2-7. One preferred adjustment screen 52 is shown in FIG. 8, showing more traditional hearing aid settings in the text in FIG. 8. However, many lay users will have little or no interest in such more detailed control of the DSP, particularly prior to performing the cognitive training further described below.

Once the user has selected whichever one of the twenty-four playback settings sounds best, a collection of actual parameter values are plugged 50 into the DSP of the hearing assist device. The parameter values will necessarily also depend upon which particular DSP is being used and options and the sound characteristics/transfer function of the particular hearing assist device. So, for instance, by having a fifty-eight year old female user select that the voice samples in the preferred telephony ear are best understood in the "dark blue square" settings, the fitting software initially sets the DSP program settings with a frequency band gain curve, an Output Compression Limiter MPO in each channel curve, and a Compression Ratio in each channel curve to modify the amplification of voices heard by the user in a way which best draws upon the user's hearing ability for voice comprehension. The fitting software includes values for each of the amplifier parameters.

If desired, and as more data is gathered to determine the most common fitting profiles, the specific curves and algorithms used may be further individualized for different combinations of age, gender and preferred telephony ear, and possibly for additional preliminary data input (cause of hearing loss, weight, ear size, etc.) by the user. Similarly, as more data is gathered, any of the parameter settings which in the preferred embodiment do not change based on the user input/selection of color/shape (i.e., DSP parameters other than frequency-gain curve, compression ratio in each channel, and compression limiting/MPO in each channel) may alternatively have differing values as a function of the user selections. It should be understood that the specific parameter settings are dependent upon the specific amplifier/hearing assist device being fitted, and that the values for any playback curve and parameter set can and will change as more data is gathered about the efficacy of the selected values for all the amplifier parameters that are applicable to improve intelligibility and cognitive training.

In a separate aspect, the DSP setting software application shown in FIGS. 2-8 is connected to a central, cloud-based database. Every change of settings made by the computing devices of users in the field, is stored inside the cloud database. Preferably, the computing device includes its own microphone, and the cloud database also stores a signal of the sound environment in which the setting change was made. The central database is used, in one instance, for individual improvements and adjustments to the algorithms converting between the selections shown in FIGS. 3-7 and in FIG. 8 and the parameter values plugged into the DSP.

Figure 9:
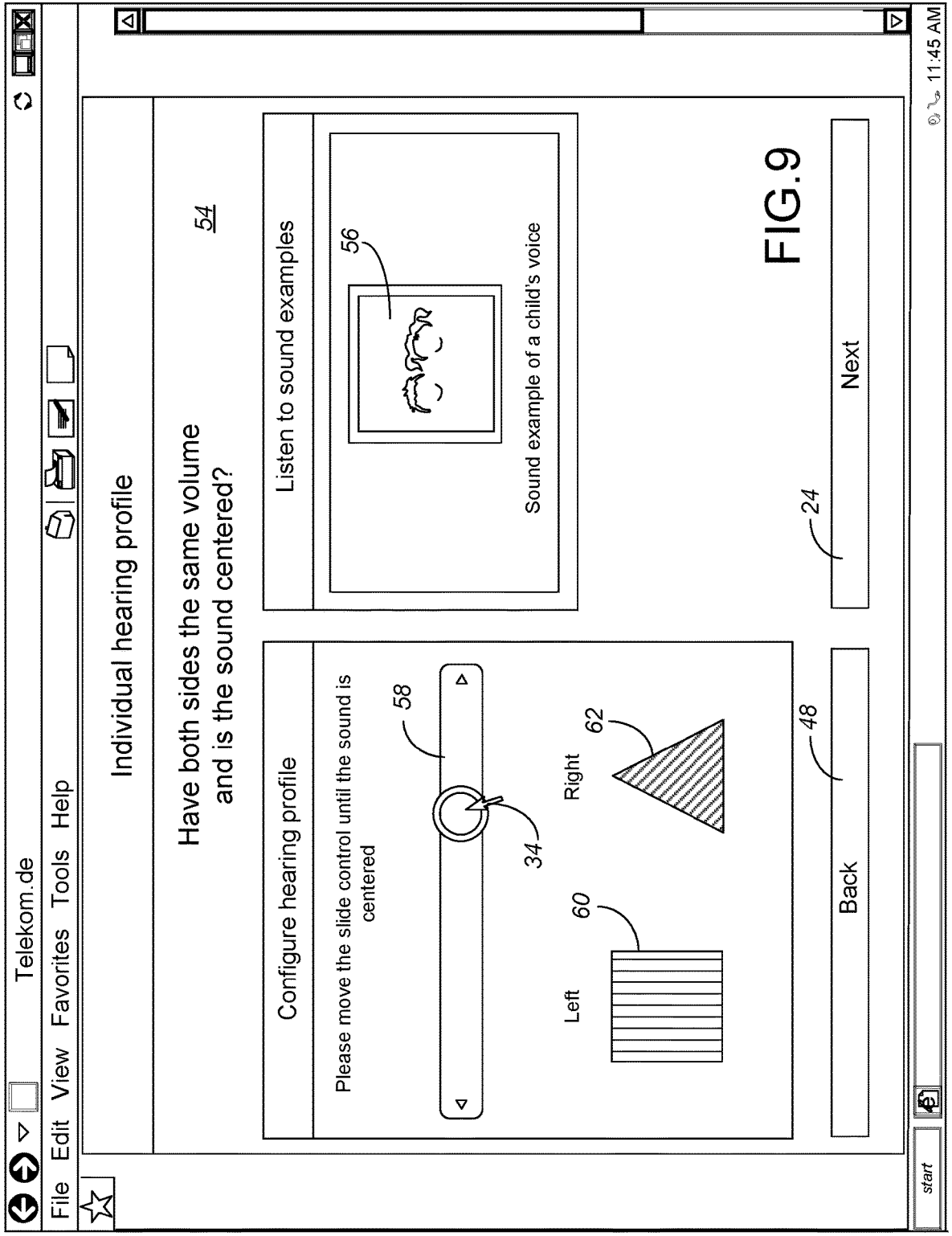
FIG. 9 is a screen shot of a balance screen which can be used in the method of FIG. 1.

After performing the voice comprehension testing of each of the two ears, the user proceeds to balance testing 54 as shown in FIG. 1. The preferred balance testing is again performed with a computer screen 54, as depicted in FIG. 9.

The user plays sound samples 56 and balances the sound heard in each ear by adjusting the slider position 58. The balance testing 54 is particularly important for users who will be wearing two hearing assistance devices, one for each ear, so the DSP settings of the two devices are determined collectively rather than determining settings for each device individually. The results of the balance testing are also used to adjust the hearing device parameters as determined by the simplified hearing profile system testing. The preferred balance testing is performed based on playback 56 of a child speaking, heard in both ears, also providing a confirmatory display and allowing the user to verify the separate setting 60, 62 previously selected for each ear using the earlier screens as shown in FIGS. 2-7. Alternatively, for some patients a single hearing assist device may only be worn in one ear, in which case the testing of the other ear and the balance testing 54 steps are omitted.

As an alternative to conducting the hearing test to assess hearing in each ear for which the hearing assist device being fitted by using a sound signal output by the computer (including through calibrated headphones), the hearing testing of the present invention could be performed by directly using the hearing assist device(s). The user would wear the hearing assist device(s), preferably having a wired or wireless structure in place to communicate with the hearing assist devices. For instance, the computer could communicate an audio signal to the hearing assist device (essentially, transmitting a digital version of the signal played on the calibrated headphones) such as using a telecoil or Bluetooth type transceiver or a wired in-situ connection, with the receiver (speaker) in the hearing assist device itself generating the audio wave in the user's ear. As another alternative, a single version of a female voice and a single version of a male voice could be generated by the computing device and picked up by a microphone in the hearing assist device, with the computer then using a wired or wireless transmission of DSP parameter changes, so the amplification characteristics of the receiver (speaker) -generated sound of the hearing assist device changed in real time as the user clicks and drags the slider 32 between red circle 40 and other color/shape positions. In all these other approaches, the user would still be self-conducting a hearing test is based upon intelligibility of speech using a plurality of sound processing parameter curves and selecting the sound processing parameter curve which provides the best intelligibility of speech.

In some aspects, the present invention can be practiced merely by storing the parameter values as determined above for operation of the DSP in use. The method of transmitting the calculated DSP parameter values to the hearing assist device and storing the parameter values in the DSP can be either through a wired or wireless transmission as known in the art, and is not the subject of the present application.

More preferably however, the simplified hearing profile system testing described above is really just a first aspect of the present invention that simplifies the steps previously performed by audiologists so the user can self-fit the hearing assistance devices. After taking the simplified hearing profile system testing 26 concluding with the balance testing 54, the user preferably proceeds with a performance test 64 to assess aural cognitive abilities of the patient, with preferred embodiments further explained with reference to FIGS. 10-18. Like the hearing testing 26, 54 described above, the performance test 64 to assess aural cognitive abilities of the patient could be performed using the sound output by an in-situ hearing assist device (not shown), but more preferably is performed using calibrated headphones (not shown) directly connected by wire to an audio jack (not shown) of the computing device.

Figure 10:
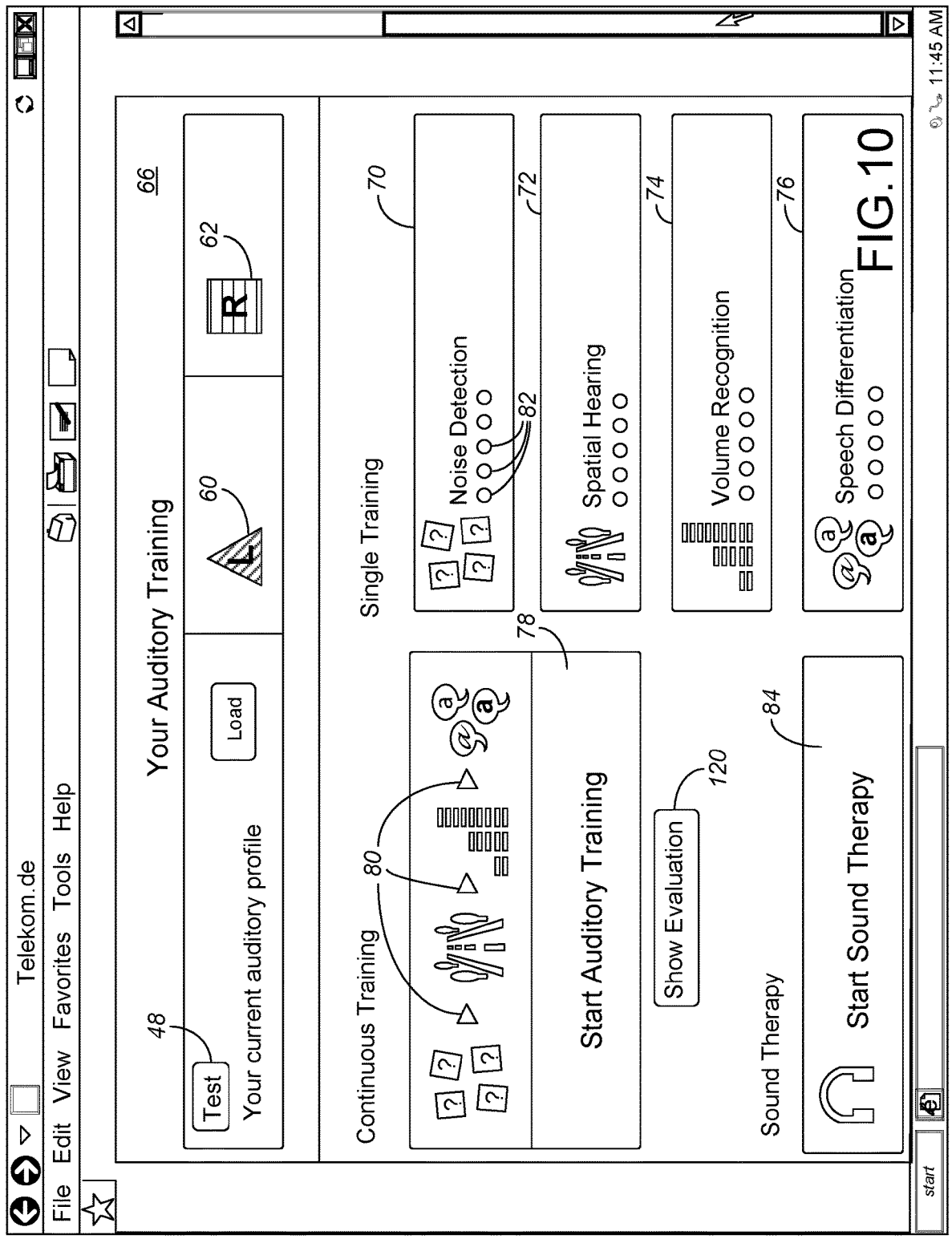
FIG. 10 is a screen shot of a control screen for the preferred cognitive training/testing protocols in the method of FIG. 1.

FIG. 10 shows a control screen 66 for the preferred performance testing 64 to assess aural cognitive abilities of the patient. The control screen 66 uses the word "training" rather than "testing" because the user's act of taking the test helps to increase the user's aural cognitive abilities, but it is the score the user achieves on the various tests which determines the subsequent training and hearing assist device usage protocols recommended for that particular user. While various screens use the word "training", "training" is synonymous with "testing" when the user's cognitive abilities are being quantified using the computer training screens.

The control screen 66 allows the user to individually select which type of performance testing to run, with four buttons 70, 72, 74, 76 which can be clicked on for each of the four preferred tests, further explained with reference to FIGS. 11-13 and 15-18. The control screen 66 includes a clickable button 78 which alternatively allows the user to serially run all four preferred performance tests in the preferred order. The preferred control screen 66 shows the setting 60, 62 for each hearing aid, and allows the user to go back 48 to the simplified hearing profile system testing of FIGS. 2-7 and 9. With the ability to go back and to proceed through the testing in different orders, each of the clickable buttons 70, 72, 74, 76, 78 for running the tests may have indicators, such as the arrows 80 or the radio dots 82, which light or change color to show the user's progress through the testing/training on this computer session. If desired, the computer can store the user's progress through the various testing protocols, so a session for any given user can be paused and then restarted hours or days later. The control screen 66 also includes a clickable button 84 which allows the user to play sounds for hearing therapy (to rest and relax the brain), further explained with reference to FIG. 18.

In one embodiment of performing the testing to assess aural cognitive abilities, the user wears hearing assist devices for one or both ears (as applicable), and the sound is merely output on the computer, tablet or smartphone speakers. This is in contrast to the preferred hearing testing using calibrated headphones. Switching from the headphones to use of the hearing aids is another reason that users inherently understand the "training" label as directed to the cognitive portion of the method and as being very different from the hearing testing. Alternatively, the sound signal can be directed to the hearing assist device via a wired or wireless transmission and bypassing the microphone of the hearing assist device, or the sound signal could be played using the headphones, but in either case the transfer function of the hearing assist device (i.e., particularly the frequency-gain curve, compression ratio in each channel, and compression limiting/MPO in each channel determined by the hearing testing procedure/algorithm for each ear) should be applied to the sound before it is perceived in each ear by the user. While variance in head direction is minimized because the user is looking at the computer screen, use of the headphones, or use of the hearing assist device(s) while bypassing its (their) microphone(s), is advantageous because the balance of sound between the two ears does not depend in any way on the direction the user's head is facing at that particular time.

Figure 11:
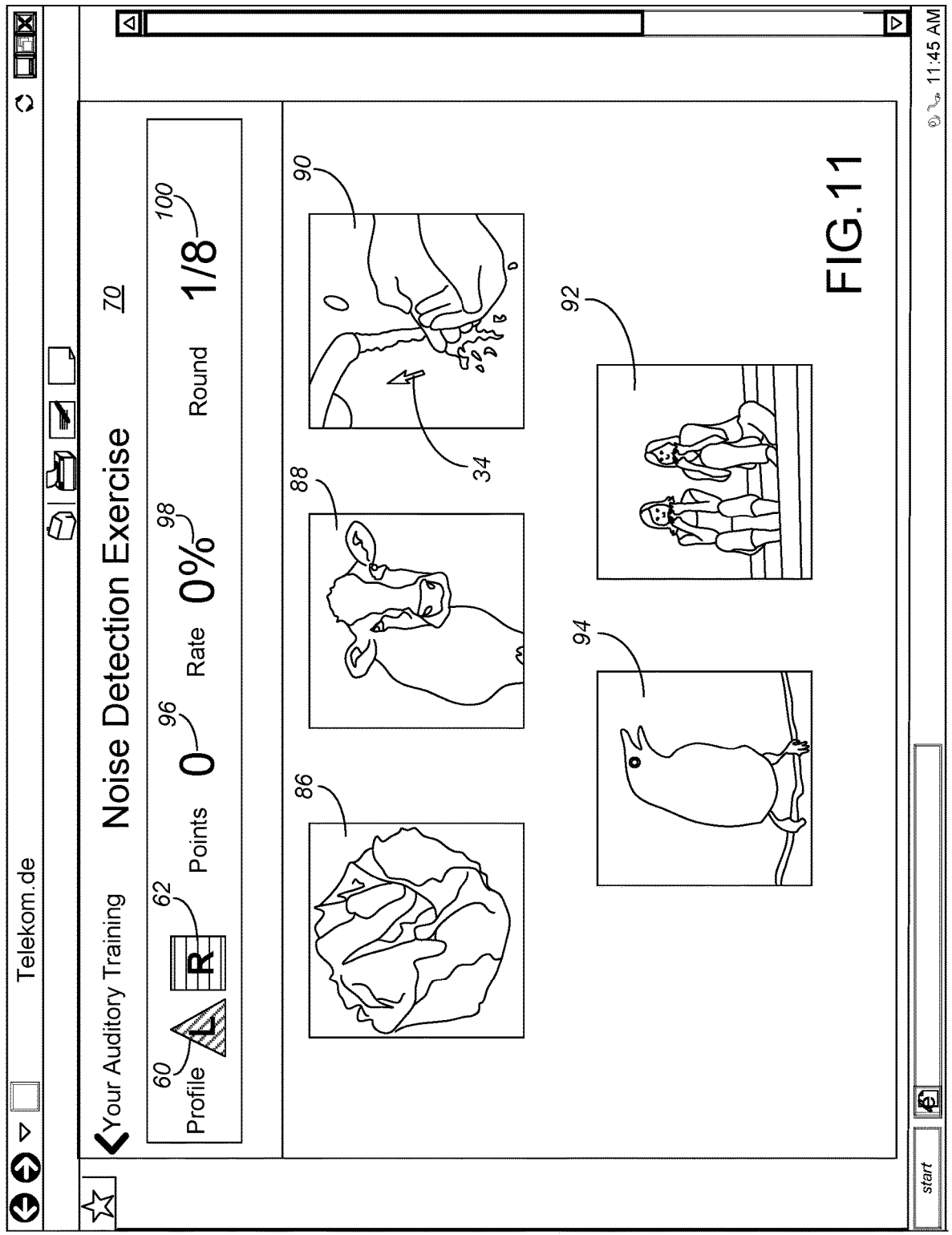
FIG. 11 is a screen shot used in a first preferred type of cognitive training/testing.

FIG. 11 represents a first performance testing 70 for the present invention which involves the ability to identify or detect what are normally considered background noises. A background noise (non-speech) is played which the user would like to be able to hear and distinguish. This test is primarily intended to assess the user's cognitive memory. During the duration that the user has been hard-of-hearing, the cognitive links in the user's brain may have degraded or been lost, i.e., the user may have essentially forgotten what these sounds sound like. As depicted in FIG. 11, preferred sounds for this cognitive memory testing 70 include paper crumpling 86, a cow mooing 88, water trickling 90, human whistling 92, and a bird chirping 94, with in this example the user's mouse 34 clicking on the water trickling 90. Typically a patient's cognitive memory degrades worse for sounds that are substantially within the frequencies that hearing has degraded most, and for most patients this will be in the high frequency registers. Accordingly, the sounds selected for use in testing 70 will be characterized as having different frequencies but focused on high frequency sounds. For instance, water trickling, chirping and whistling are concentrated in higher frequencies than a cow mooing. The sounds played for the cognitive memory test 70 should also vary in how smooth or harsh (how many clicks, points per second, and how quickly different frequencies change intensity) the various sounds are. For instance, whistling is smoother than paper crumpling. The sounds played for the cognitive memory test 70 can also vary in volume, and/or in rate of volume change. Workers skilled in the art will be able to select numerous additional sounds, identifiable by most people with perfect hearing, which can be used in performing this cognitive memory test. Upon hearing and identifying the sound, the user then selects the image 86, 88, 90, 92, 94 which corresponds with the background noise being played, such as by clicking on the image button. The user's response can be assessed both in whether the user correctly identifies the sound and in how long it takes for the user to click the correct button 86, 88, 90, 92, 94 after the sound begins playing.

Note that different classes of people, particularly different types of experts, can have very different cognitive memory bases, and that some fields of endeavor rely on cognitive memory much more than others. The cognitive memory test 70 can accordingly be specialized for different classes of people. For instance, the cognitive memory test 70 for amateur or professional ornithologists could be entirely based on chirping of different species of birds. For such amateur or professional ornithologists, the loss of the ability to distinguish between bird species based on the sound heard can be emotionally traumatic, and be a primary motivator for the individual to want to use the hearing assist device(s). Such specialized cognitive memory tests, if sufficiently developed, can then be used as training tools for individuals to enhance their cognitive memory without regard to hearing loss. For instance, ornithology students can perform the training to learn to identify different species of birds based on the sound of chirp each species makes. Another example would be automobile mechanics, using the sounds of an engine or automobile in diagnosing a problem to be fixed or an automobile part to be replaced.

The preferred noise detection exercise screen 70 of FIG. 11 shows the hearing testing setting 60, 62 for each hearing aid. The preferred screen also provides immediate feedback to the user performing the training, including showing a cumulative score 96 and a rate 98 (which can be either the rate correct as a percentage of tries, the rate at which answers are being given as a function of time, or a combination of both), and also an indication of which round 100 of testing/training 70 is begin performed.

Figure 12:
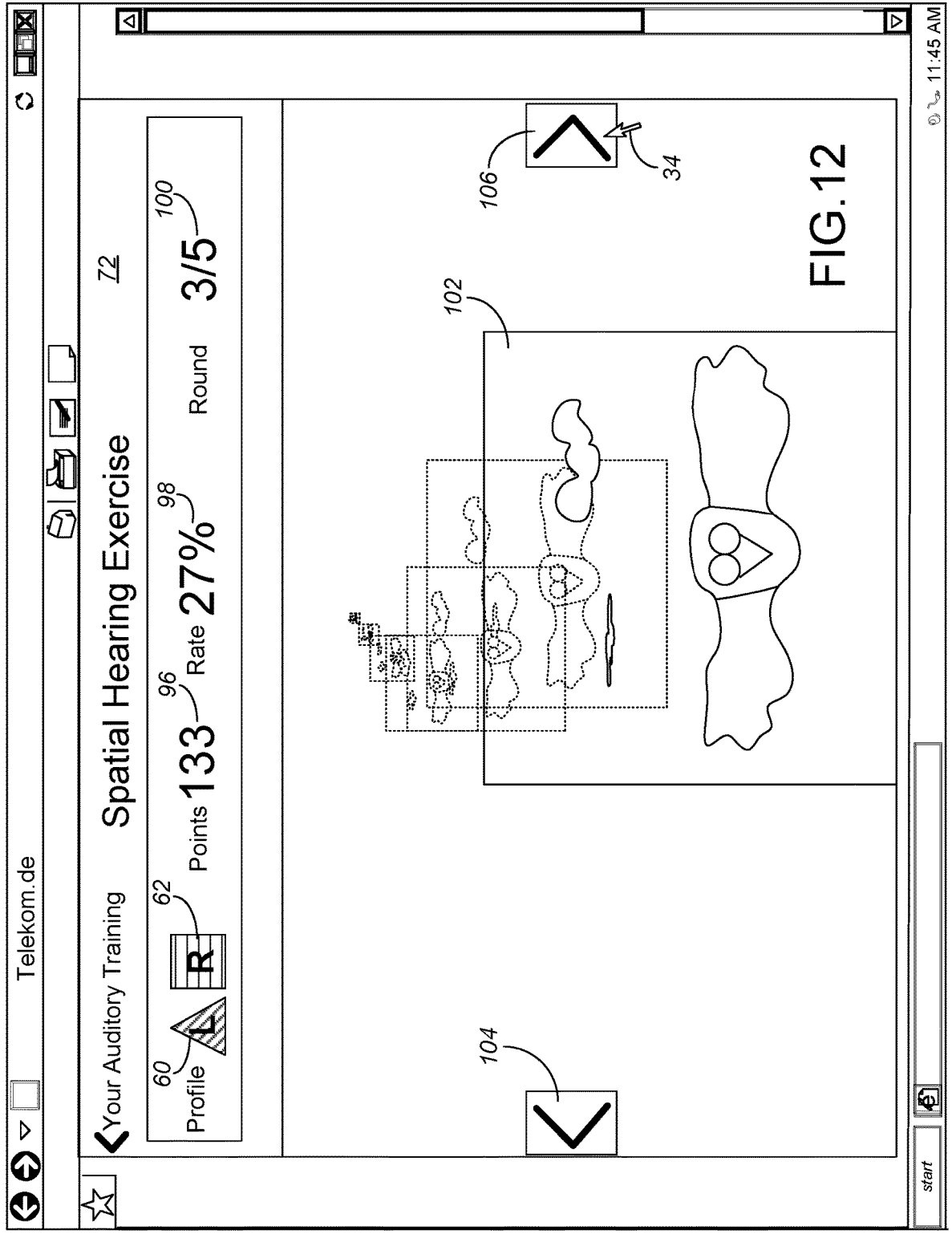
FIG. 12 is a screen shot used in a second preferred type of cognitive training/testing.

FIG. 12 represents a second performance testing 72 for the present invention which involves the ability to determine sound source movement, a type of spatial hearing. This test 72 assesses what can be referred to as "lateralization". A sound is played (such as of a bird flying, or a mosquito buzzing), with the balance and fade continually changing as a function of time during playback so the sound seems to approach and then pass the user. Preferably the computing device used for this test 72 includes stereo or surround sound speakers. Particularly when generated by a speaker (set) from in front of the user, a doppler effect may be coupled with changes in volume to further give the sense that the sound source has passed by the users. When passing the user, the sound source passes either to the user's right or to the user's left. The testing 72 requires the user to determine on which side (right or left) the sound source passed. The testing 72 may also assess how accurately the user can judge the instant when the sound source is at the user, with the user attempting to click when the sound source is closest. In the example of FIG. 12, the sound being played is the sound of a bird 102, which can either being chirping or the sound of its wings, moving and coming at the user, with the dashed lines indicating the image of the bird 102 at earlier points in time to visually correspond with the sound being heard. The screen 72 may include clickable buttons 104, 106 to indicate which side the sound passed on, or the keyboard can be used for the user to enter results. Alternatively, or as an additional portion of this spatial hearing test and training, the mouse 34 can be used as an input for the user to control the position of the bird image on the screen, attempting to match with the positional location of the sound being heard as played through the stereo speakers.

The various sounds being played on different attempts by the user change in the amount and rate of balance/fade change, i.e., some testing rounds have sounds which cognitively seem to pass far to the right or left of the user and passing quickly, whereas the next testing round might have a sound which cognitively seems to pass very close to the user and passing slowly. The sounds played for the source movement test can also vary in peak volume, in primary frequencies, and in smoothness.

Figure 13:
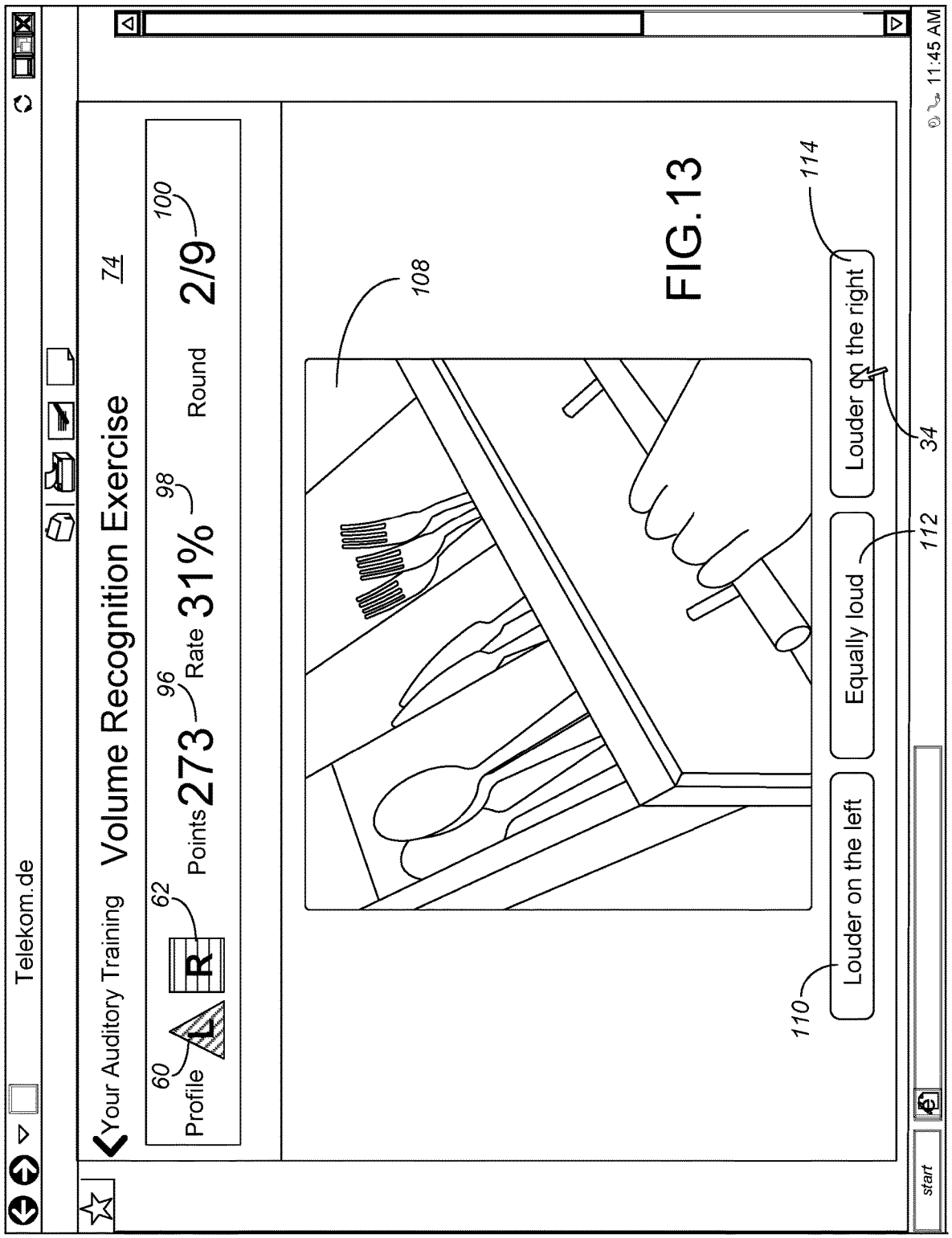
FIG. 13 is a screen shot used in a third preferred type of cognitive training/testing.

FIG. 13 represents a third performance testing 74 for the present invention which involves the ability to determine sound source direction without movement. In this test 74, a sound is played, and the user identifies the direction (right or left) from which the sound came. The sounds played for testing sound source direction without movement 74 primarily differ in volume, and can be provided with or without other background noise. For instance, in the example of FIG. 13, the user can attempt to identify the direction of the silverware clinking, which can with or without other noises such as music or indistinct conversation. The other background noises can also be provided directionally, such as silverware clinking on the right while music plays on the left. The preferred screen 74 includes an image 108 of the sound to be distinguished, with a clickable button 110 if the sound comes from the left, a clickable button 112 if centered, and a clickable button 114 if the sound comes from the right. The sounds played for testing sound source direction without movement can also vary in duration, in primary frequencies, and in smoothness. Again the computing device used for this test 74 preferably includes stereo or surround sound speakers, and the various sounds being played on different rounds can also change in perceived distance to the right or left.

As an addition to (i.e. for some of the rounds) or as an alternative to using non-speech sounds to determine sound source direction without movement, speech can be used, with the user asked to identify the direction of speech over other background sounds. As one example, the user can be played three simultaneous conversations, two female and one male, and asked from which direction the male conversation comes.

Figure 14:
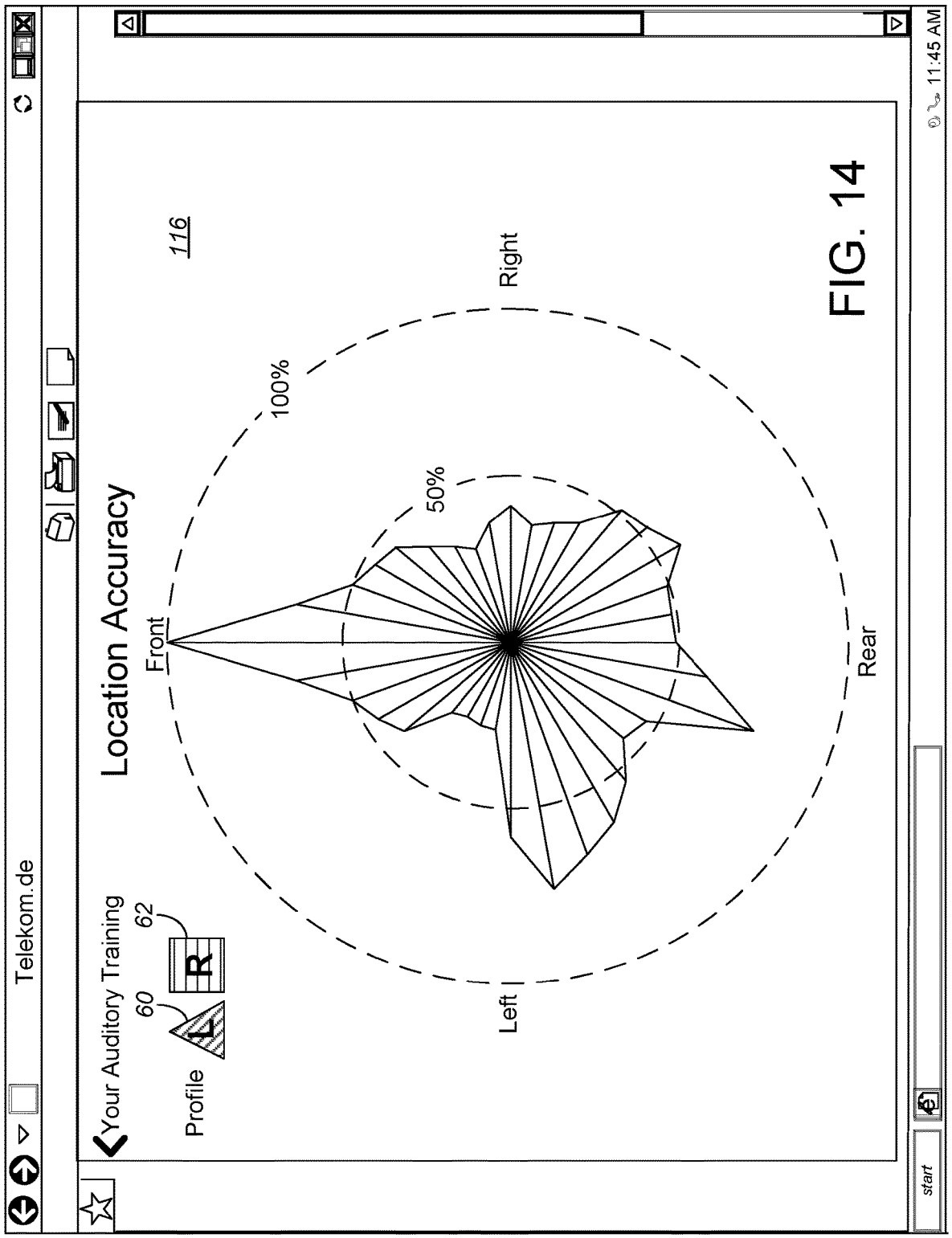
FIG. 14 shows an example of a graphical analysis of the results of the cognitive testing of FIG. 13.

FIG. 14 shows one example of a graphical analysis 116 of the results of the performance testing of FIG. 13. The user's responses to numerous rounds of testing are compiled, and graphically displayed to show the percentage of correct answers identified by the user as a function of the direction (balance and fade) of the sound played. The various graphs are preferably available by clicking on the "graphs" button 118 in the adjustment screen 52 of FIG. 8, and may be available through clicking on the "show evaluation" button 120 in the control screen 66 of FIG. 10. This particular example shows a user who does a very good job of recognizing the directionality of sounds played in front of her, but not a good job of recognizing the directionality of sounds played from her right, even when hearing was equally corrected in both ears. Such variances can involve both a preferred telephony ear and a loss of aural cognition from the duration of being hard of hearing. In most cases, a patient's results significantly improve over time as a result of practice by taking the testing 74 of FIG. 13, particularly if the training 74 occurs using the properly set hearing aids over a period of days. Screens such as FIG. 14 can be used not only to better understand the cognitive loss and then improvement of this particular patient, but also as encouragement so the patient can understand how training using the properly set hearing aids has lead to better performance, resulting in a much better adoption rate and satisfaction over use of the hearing aids. Other graphs can chart, for instance, a listing of frequencies versus the percentage correctly identified by the user, and/or a comparison between frequencies being identified versus decibel level for accurate identification. Frequency graphs can preferably be provided either linearly or logarithmically. Other graphs can display the frequencies played by any of the sound samples as a function of time as the sound sample plays. The preferred software for the present invention thus includes screens to graphically display the performance, and particularly the improvement, which occurs as a result of the cognition training 64 of the present invention. Some users will have little interest in understanding the particular cognitional ways in which their brain is learning once again to correctly understand sounds, and may never use the graphing and analysis provided by the present invention, whereas other users will find the information presented very valuable in better understanding their hearing cognition training 64.

FIGS. 15-18 show a fourth performance testing 76 for the present invention which involves the ability at different relative volume levels to distinguish speech in the presence of noise. FIG. 15 is an explanation screen 122 explaining to the user what the testing/training consists of and how to perform the testing/training. Each of the hearing testing 26 and the first three cognition performance tests 70, 72, 74 described above can include similar explanation screens (not shown).

Figure 16:
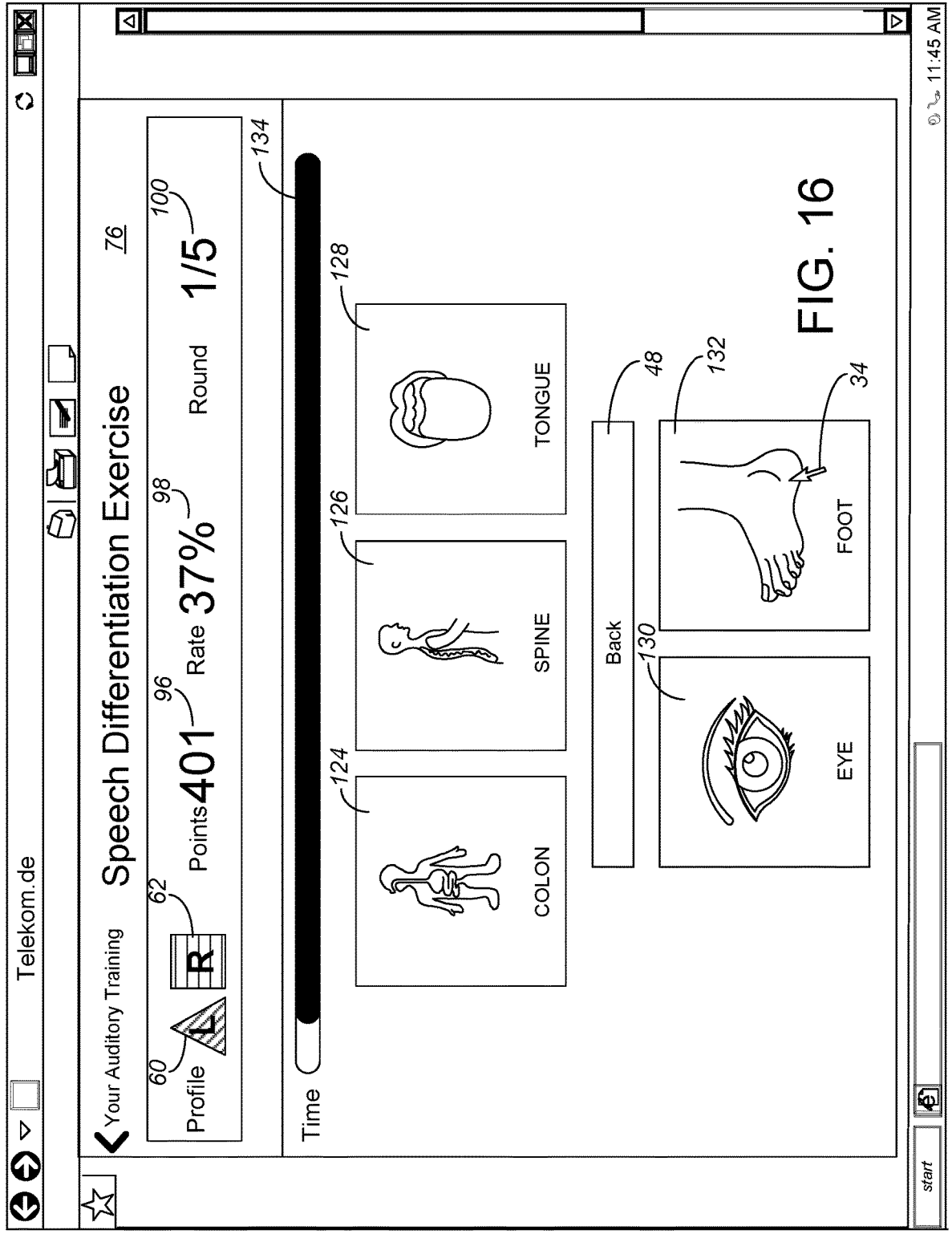

FIG. 16 shows a first round of the speech differentiation testing/training. As the relative volume of the speech increases, the user is timed in his or her selection of the topic of the speech. In the first example, the topic options were anatomical, e.g., "colon" 124, "spine" 126, "tongue" 128, "eye" 130 or "foot" 132. Preferably each clickable answer button 124, 126, 128, 130, 132 includes an image of the topic option, reinforcing that the objective is understanding speech content, not merely identifying or matching words. The preferred embodiment includes smaller words for each of the topic option buttons 124, 126, 128, 130, 132, avoiding any ambiguity over what the image represents, but the words in the topic option buttons 124, 126, 128, 130, 132 can be omitted. A timer 134 can be shown on screen.

Figure 17:
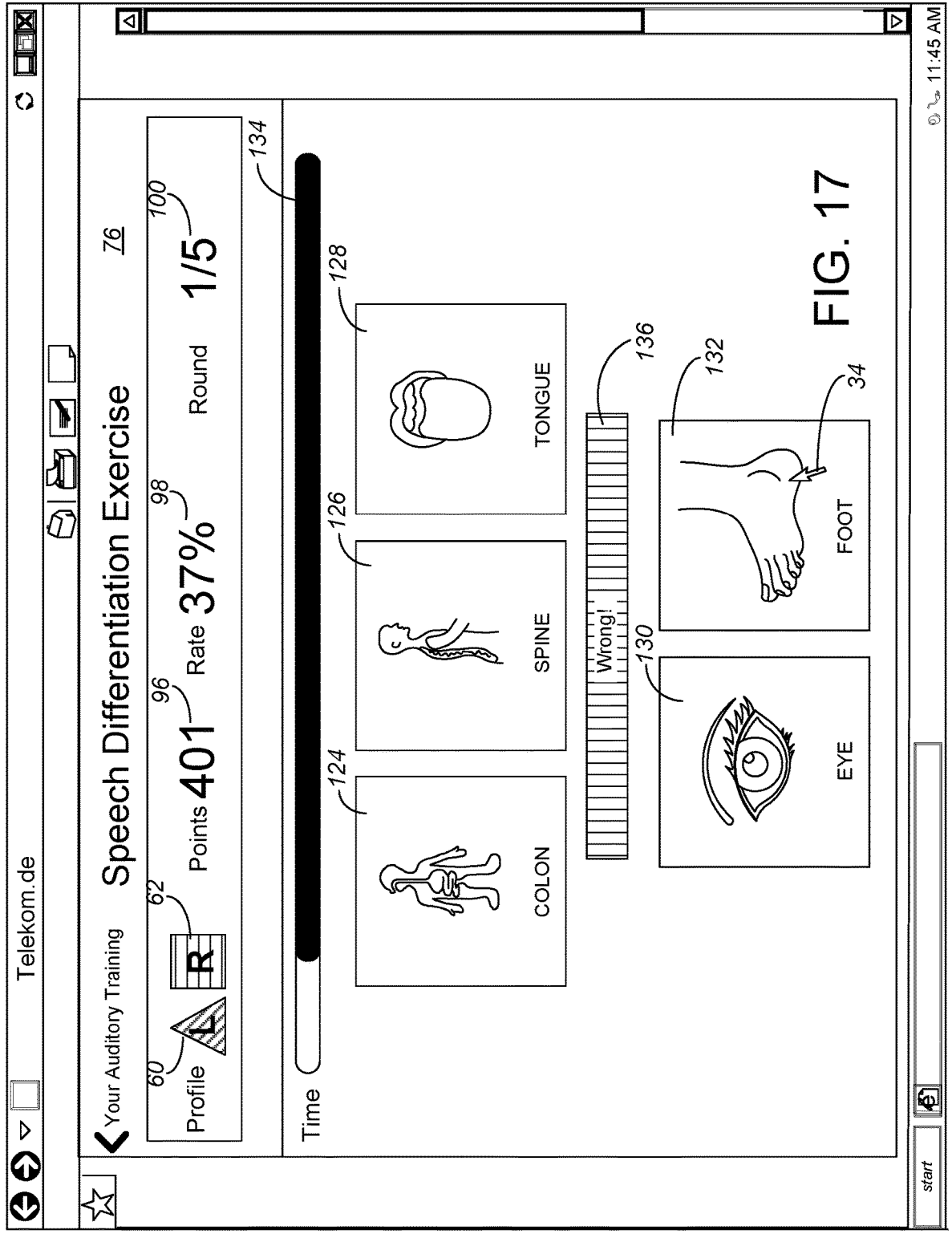

In FIG. 17, the user quickly responded believing that the topic of the relatively indistinct speech being heard was a foot, but the response was incorrect. The preferred software provides a mechanism, such as changing the back button 48 into a red-colored "WRONG!" display 136 or a buzzer, for immediate feedback to the user about the accuracy of the results. For any of the previously described training-tests 70, 72, 74 for which a correct or incorrect answer is given (as opposed to merely timing of the user's response), the user can be given similar immediate feedback.

Figure 18:
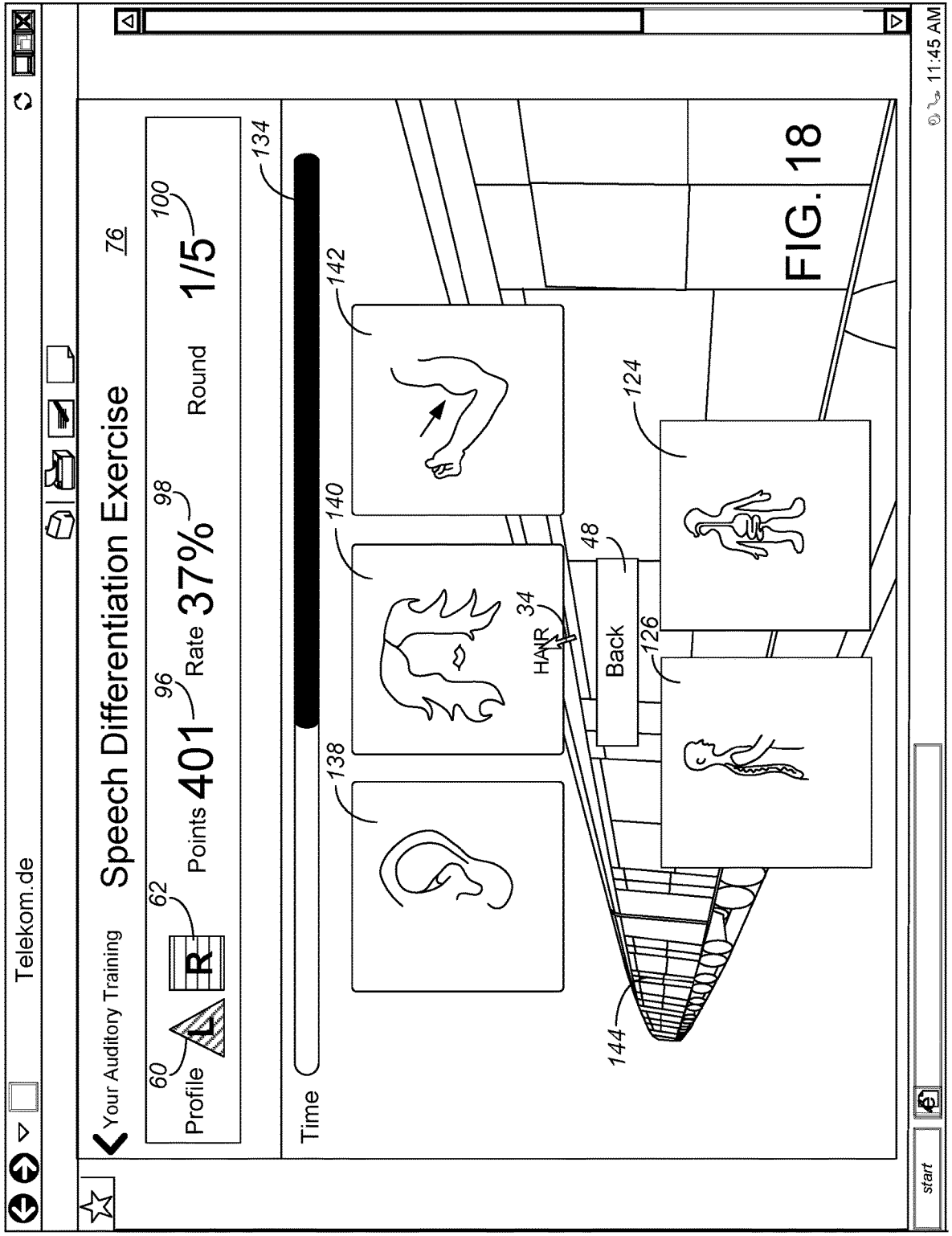

In a next example shown in FIG. 18, the options are once again anatomical, this time "ear" 138, "hair" 140, "muscle" 142, "spine" 126 and "colon" 124. However, to further reinforce that the objective is understanding speech content, not merely identifying or matching words, the corresponding words only appear on screen when the user mouses over that portion of the clickable button. For FIG. 18, the background noise is changed to the sounds heard from a train. In this case, the background noise topic 144 is also graphically present to the user while performing the test. Almost without the user realizing, this further helps improve the cognitive relearning of the patient to identify and cognitively remember the background noise, while at the same time reteaching the cognitive separation ability of the user to distinguish speech over such background noise.

This type of performance testing represented in FIGS. 10-13 and 15-18, and particularly the speech over noise recognition performance testing represented in FIGS. 15-18, is important to continue to monitor and adjust as the user continues use of the hearing assistance device(s). Though not commonly realized, as people become hard of hearing, part of the degradation is due to a loss of cognitive ability to distinguish sounds that they can no longer hear, i.e., part of the hearing aid fitting problem is due to unlearning which occurs in the user's brain rather than merely a lack of ability of the user's ears. The same sort of loss of cognitive ability could occur, for instance, if a person went for years in a silent environment without hearing speech but without any loss of hearing ability. Even when the hard-of-hearing user's ears are restored by the hearing aid profile in the hearing assist device, the user may need to retrain his or her brain to distinguish between sounds that can now be heard again and to regain speech understanding.

In yet another aspect, cognitive performance testing results are also transmitted and stored in a central cloud database as additional users perform the testing/training. The central cloud database is analyzed and used to improve the algorithms for all users of the present invention in determining DSP parameter values, by analysis and comparisons between the cognitive scores and the settings used by multiple users.

A further and important aspect of the present invention is the non-testing training regimen which makes use of the cognitive hearing assessment, further explained with reference to FIG. 1. The amount of cognitive loss can be measured through the testing 70, 72, 74, 76 represented in FIGS. 10-13 and 15-18. Once measured, the measurement can be summarized or categorized on a scale of 0 through 7, counting back through the age in years when most people learn to distinguish between speech sounds. The cognitive loss categorization index can be thought of like an "A" through "F" letter grade in U.S. schools, which sums up the total number of points earned on all the assignments during the term; in FIG. 18, the score "401" is out of a greater number of possible points, and how much cognitive loss is represented by the 401 score necessarily depends upon how many rounds of training are performed. For example, a score of 401 out of 425 might correlate to a cognitive loss category of 0, whereas a score of 401 out of 825 might correlate to a cognitive loss category of 4. The stage of cognitive loss is then used to modify the parameter settings of the hearing assist device(s), or more importantly, to ascertain how the usage (and DSP parameter settings during such usage) of the hearing assist device should be adjusted over time so the user can most easily relearn how to distinguish between sounds using the hearing assist device(s). Devising the hearing device usage regimen to best improve-over-time in cognitive ability to distinguish between sounds is a significant aspect of the present invention.

The cognitive testing gives an indication of how far the user's cognitive ability to understand speech has degraded. If the patient has a severe loss of cognitive speech recognition ability (particularly those users who test out to a cognitive loss category of 5 to 7), use of the hearing aid in any sort of noisy environment is likely to still leave the user frustrated with a poor ability to understand speech. Instead of programming the hearing aid for everyday/noisy situation use, the user is told NOT to regularly wear the hearing aid. Instead, a program of parameter settings 146 ("Journey") is installed in the hearing aid for the user to conduct cognitive training, on their own time, using their own interests and without assessment during training. At present, the preferred embodiment includes four levels or different sets of training settings 146 which can be programmed into the DSP and regimens which should be followed: one for severe cognitive loss 148, in the cognitive loss category of 5 to 7 years unlearned; a second for medium cognitive loss 150, in the cognitive loss category of 3 to 4 years unlearned; a third for mild cognitive loss 152, in the cognitive loss category of 1 to 2 years unlearned; and a fourth for essentially no cognitive loss 154.

The preferred non-assessment cognitive training involves listening to voices in a low noise environment. For best results, such cognitive training should be performed for a duration in the range of 5 minutes to 180 minutes during a day. While speech in low noise environments can be provided in a number of settings, typically the easiest and most entertaining (and hence best followed and tolerated) training is performed by watching TV with the hearing aid in the cognitive training program of DSP parameter settings 146, such as for about 90 minutes a day. The Journey program of DSP parameter settings use a very low compression ratio, which is tolerated in the low noise environment. The Journey program of DSP parameter settings modifies and changes the baseline DSP parameter settings (the green triangle 60 and dark blue square 62, for instance), which were identified in the hearing testing mode of FIGS. 2-9.

Figure 19:
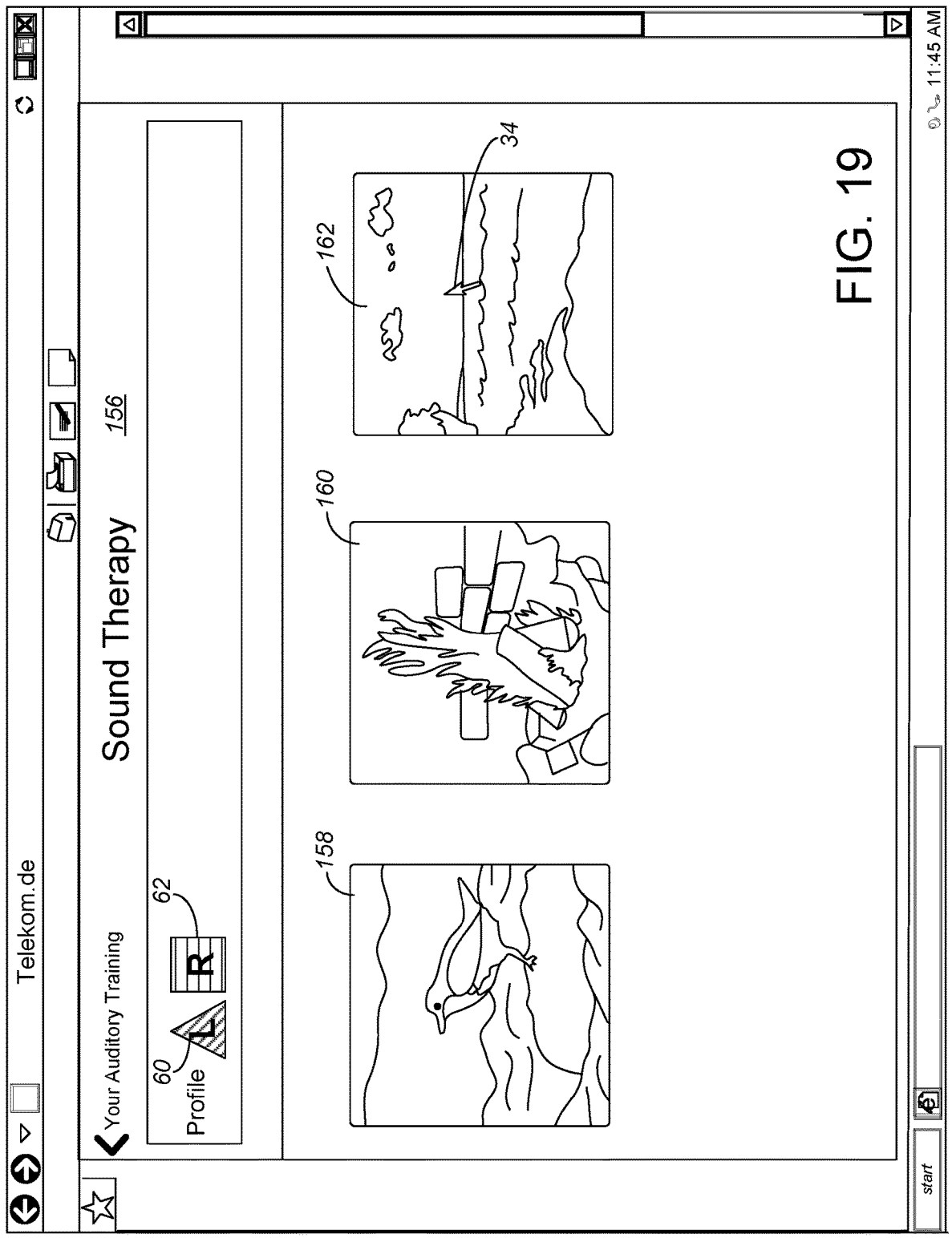
FIG. 19 is a screen shot used in sound therapy in the present invention.

After this concentrated work on understanding TV voices, the cognitive hearing portions of the user's brain are typically exhausted. For adoption rates of the hearing assist devices to be high, care must be taken to not overload previously-underused-portions of the user's brain too quickly. An adequate period of relaxation of the cognitive-hearing portions of the brain is integral to proper training. FIG. 19 shows a screen shot 156 of a portion of the computer system which can be used for the proper relaxation or hearing therapy, which can be reached from the control screen 66 of FIG. 10 by clicking on the hearing therapy button 84. In this example, the relaxation sounds which can be played include bird and breeze sounds 158, campfire sounds 160, and ocean shore sounds 162. Alternatively, tapes and/or CDs of relaxation sounds are commonly commercially available, often used for sleep aids. Immediately following use of the self-directed non-assessed training sessions, the patient listens to relaxation non-speech sounds for a duration of at least 5 minutes, so the patient can rest the cognitive speech/noise distinguishing portion of the brain. In the most preferred regimens, the user spends about 30 minutes listening to relaxing, natural sounds, using the hearing assist device with its DSP parameter settings in the cognitive training program.

After the user has performed this daily cognitive training regimen for a period of time, typically 3 to 28 days and preferably in about a week, the user repeats the cognitive testing 70, 72, 74, 76. Usually after a few weeks the user's cognitive ability score improves to the next cognitive loss category level.

If the user initially has, or after several weeks of training improves to, a medium or moderate cognitive loss 150, the user is told to use the hearing aid with its baseline DSP settings during day to day activities. At this point, the hearing aid with its baseline settings provides enough benefit in voice recognition performance that the daily wear will not prove exceedingly frustrating. Day to day activities typically occur in what are considered regular or high noise environments. For best results, the usage of the baseline DSP settings in the day to day activities should be for a duration of at least 15 minutes during a day. Separate from the baseline settings, a new set of cognitive training parameters 146 are installed in the hearing aid in a modified cognitive training program ("Journey 2"). On most hearing aids, the user can switch between the baseline DSP parameter settings and the Journey 2 DSP parameter settings using a simple switch or button on the hearing aid, or perhaps by using a hearing aid remote control. The Journey 2 cognitive training DSP parameter settings are similar to the Journey cognitive training DSP parameter settings, but increases the compression ratio. Once again the user is told to perform cognitive training (listening to voices in a low noise environment, such as by watching TV) for a duration in the range of 5 minutes to 180 minutes and most preferably about 90 minutes a day, followed by a period such as about 30 minutes of relaxing listening. In other words, the user uses the baseline settings for most of the day, but performs cognitive training with a different set of hearing aid settings and while listening to voices in a low noise environment for a limited time each day. This results in the patient's brain being presented with more noise relative to speech and such that the patient's brain better learns to distinguish between speech and noise when using the hearing assist device. After the user has performed this daily Journey 2 cognitive training regimen for a period of time (typically 3 to 28 days and preferably in about a week) including wearing the hearing aid during day-to-day activities, the user repeats the cognitive testing. Usually after a few weeks the user's cognitive ability score continues to improve to the next level.

Once the user's cognitive loss score falls into the "Mild" category (more similar to the speech cognition ability of a 5 to 6 year old), the cognitive training parameter settings are again adjusted. The Journey 1 cognitive training parameter settings are similar to the Journey 2 cognitive training parameter settings, but with a further increase in compression ratio.

Most users are, after several weeks of performing the cognitive training (concentrated listening to voices in a low noise background with high compression settings on the hearing aid) for an hour or two per day, able to significantly improve their cognitive training score, including significantly or fully restoring their ability to understand speech. At this point, the improved hearing ability made possible by the hearing aid using its baseline settings, allows the user to obtain a significant benefit in being able to understand voice, even in higher noise, day-to-day settings (the so-called cocktail party environment).

At any point during the process, as shown by the dashed line on FIG. 1, the user may want to reperform the selection of which of the twenty four voice playbacks is best heard (determining whether to switch from a blue triangle set of DSP parameters to a different set of DSP parameters) for speech comprehension. While occasionally this improves satisfaction with the hearing assist device, many users can perform cognitive training to significantly reduce cognitive loss (i.e., going from Journey 3 to Journey 2 to Journey 1 to possibly eliminating cognitive training entirely) all the while maintaining the same hearing loss profile and therefore maintaining the same baseline DSP parameter settings on the hearing aid.

In a separate aspect to improve the efficacy of the present invention, the frequency bands in the DSP are not selected at arbitrary breaks convenient to the hearing aid electronics, but rather are selected on a scale and spacing corresponding to the Bark scale of 24 critical bands. See https://en.wikipedia.org/wiki/Critical_band and https://en.wikipedia.org/wiki/Bark_scale, as rounded in the following Table I.

TABLE I

| Number | Center Frequency (Hz) | Cut-off Frequency (Hz) | Bandwidth (Hz) |
| --- | --- | --- | --- |
|  |  | 20 |  |
| 1 | 60 | 100 | 80 |
| 2 | 150 | 200 | 100 |
| 3 | 250 | 300 | 100 |
| 4 | 350 | 400 | 100 |
| 5 | 450 | 510 | 110 |
| 6 | 570 | 630 | 120 |
| 7 | 700 | 770 | 140 |
| 8 | 840 | 920 | 150 |
| 9 | 1000 | 1080 | 160 |
| 10 | 1170 | 1270 | 190 |
| 11 | 1370 | 1480 | 210 |
| 12 | 1600 | 1720 | 240 |
| 13 | 1850 | 2000 | 280 |
| 14 | 2150 | 2320 | 320 |
| 15 | 2500 | 2700 | 380 |
| 16 | 2900 | 3150 | 450 |
| 17 | 3400 | 3700 | 550 |
| 18 | 4000 | 4400 | 700 |
| 19 | 4800 | 5300 | 900 |
| 20 | 5800 | 6400 | 1100 |
| 21 | 7000 | 7700 | 1300 |
| 22 | 8500 | 9500 | 1800 |
| 23 | 10500 | 12000 | 2500 |
| 24 | 13500 | 15500 | 3500 |

The algorithms for calculating DSP parameters then focuses on having the signal in as many of the thus-selected frequency bands be amplified/adjusted to include information based on the cognitive abilities of the patient. The dynamic measurements and adjustments make sure that all available critical bands are reached. The intent is not to have an objectively accurate sound given the hearing deficiencies of the user, but instead to compensate and adjust for the cognitive abilities and current cognitive retraining of the patient.

In another aspect, even if the hearing impaired person has no measurable hearing in some frequencies, the output amplifies and provides such frequencies rather than to eliminate or minimize such frequencies in the DSP. The methodology of the present invention provides as many brain relevant signals as possible to regain the brain's ability to separate speech from noise in a natural way, not by using technical features of the DSP to minimize the brain's need to separate speech from noise. The improvement in daily situations for the patient is enormous, as the sound is natural and more akin to the learning achieved during the first years of life to separate speech from noise. The brain is also trained to not lose more patterns because of further disuse of cognitive links, such disuse having begun from being hearing impaired. The result of the present invention is, through retraining of the cognitive aspects of the brain, significantly better understanding of speech in all environments, as well as reduction of stress and reducing tiring of the brain caused in the prior art consensus methods due to interpolating through missing information.

Figure 20:
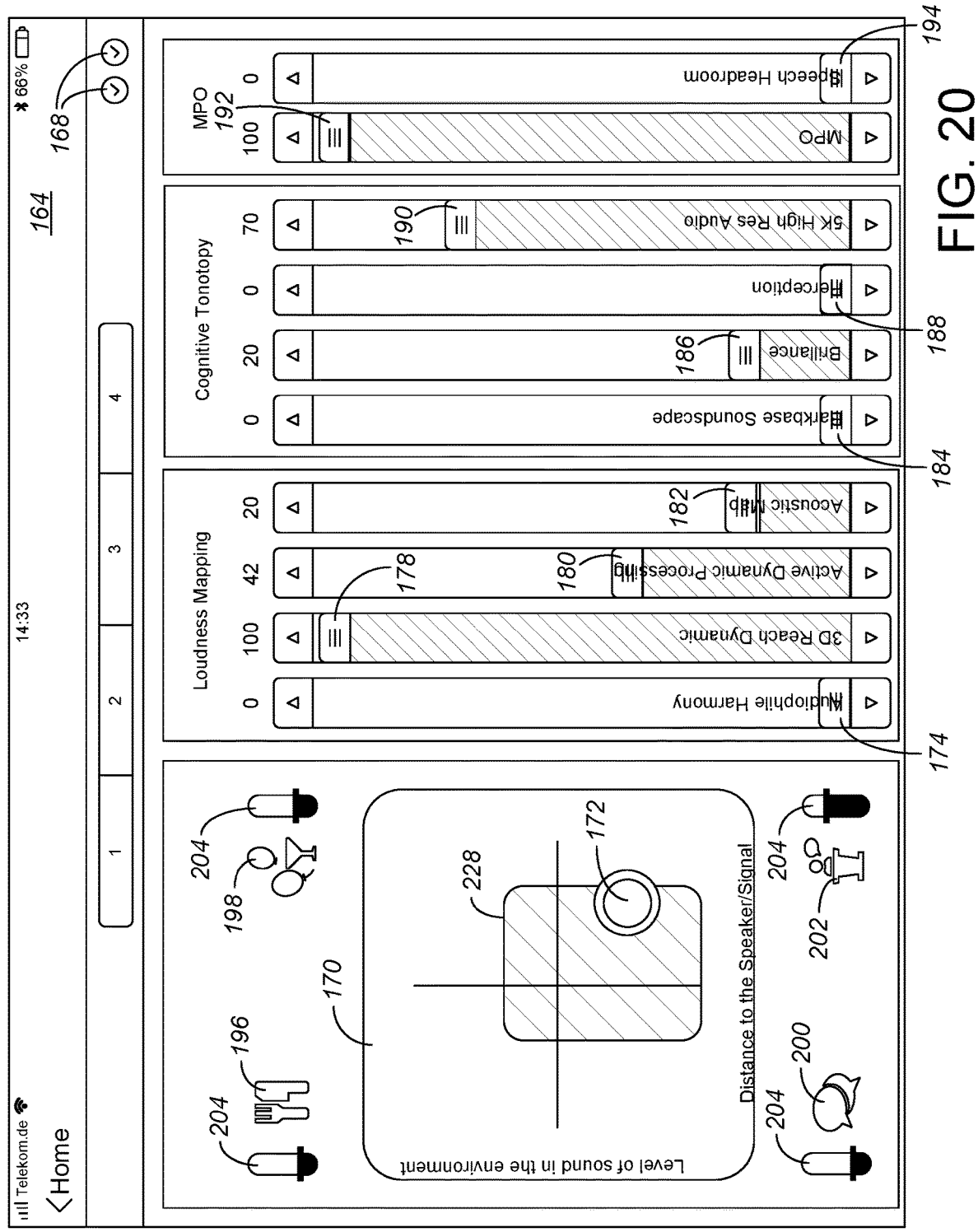
FIG. 20 is a screen shot of a second embodiment of an adjustment screen of a fitting software application running on a computing device of an audiologist or other specialist of hearing professional.

FIG. 8 shows an adjustment screen 52 of a first preferred embodiment of a fitting software application. FIG. 20 shows an adjustment screen 164 of a second preferred embodiment of a fitting software application. Most commonly, such a fitting software application 52, 164 will run on a computing device of an audiologist or other specialist or hearing professional, such as an iPad or other tablet (with screen shots 52, 164 from an iPad shown in FIGS. 8, 20 and 21), but alternatively on the audiologist's laptop computer, desktop computer, or smartphone. The audiologist application is intended to be used, for instance, in a clinic, in setting up and ongoing monitoring of a patient's progress. However, if a patient wants detailed fine tuning control over their own hearing aid(s), the patient could alternatively be given access to the fitting software application 52, 164 of either FIG. 8 or FIG. 20.

For either the embodiment of FIG. 8 or the embodiment of FIG. 20, the preferred software application 52, 164 includes one or several initial login screens (not shown), prompting the user to enter his or her individual username and password. In some embodiments, correct entry of user name and password combination will allow the user to connect to a cloud service on the Internet, either for downloading or storing appropriate control settings for the hearing aid 166 (shown in FIG. 21), for logging changes, usage or complaints, etc. In particular, the cloud service may record the patient's current or prior cognitive loss score (points) and their current or prior hearing comprehension setting (shape and color) as described previously, alone or in conjunction with the patient's age, gender, preferred telephony ear as well as the type and serial number of the hearing aid(s) being used.

After logging in, the software searches for compatible hearing assist devices which can be wirelessly connected, such as compatible hearing assist devices and accessories which are on and connectable in near field or Bluetooth range. The preferred software application shows the devices found and identified on a list (not shown), so the user can initiate wireless connection with the desired device 166. Alternatively or in addition, the list can include hearing assist devices or accessories that are already separately linked (such as via a WiFi or wired internet connection) to the cloud database.

After the user has selected the desired device 166 and the application has initiated a direct connection between the software application and the hearing assist device(s) 166, the software application may include icons 168 such as radio button(s) or green check box(es), shown on the screen 164 to indicate such a connection. The green check box(es) 168 will change to red if the connection becomes interrupted.

The finetuning provided by the software application of the present invention is different and unique, including displaying functions and settings which are new, each based on combining several hearing aid parameters for simultaneous adjustment. As shown in FIG. 8, the primary adjustments are split into four categories of "Loudness Mapping", "Cognitive Tonotopy", "MIC" (for "MICrophone") and "MPO" (for "Maximum Power Output"). As shown in FIG. 20, an alternative embodiment 164 includes a 2-D selection area at left which is a "sound map" 170, and then (primarily to save screenspace) omits the two MIC slidebars. As general categories, Loudness Mapping controls dynamics of the audio signals, Cognitive Tonotopy controls frequency and gain, MIC controls the microphone input and MPO controls the maximum output levels.

In general terms, all ten (or twelve in FIG. 8) of the slidebars are consistent with an overarching concept. When the audiologist or user pulls any of the slidebars upward, to a higher fidelity setting, the resultant changes to the DSP parameter settings result in more brain work for the patient, more differentiation of speech and better understanding. When the audiologist or user pulls any of the slidebars downward, to a lower fidelity setting, the resultant changes to the DSP parameter settings result in requiring less brain work of the patient, generally resulting in more comfort and easier listening by the patient but less understanding of speech. While slidebars are used as the control graphic in the preferred embodiments, other types of user interface control graphics (dials, numerical controls, etc.) could alternatively allow the user to control the values discussed.

The sound map 170 is a two dimensional display in which the user can drag and drop the circular cursor 172. Any location on the sound map 170 corresponds to values of several or all of the ten (in FIG. 20) parameters shown on the right. For instance, in one embodiment, as the user moves the cursor 172 on the sound map 170 at left, eight of the ten values shown on the slidebars at right all move and change, in a controlled mapping scheme. Alternatively, the user can individually adjust any of the ten parameters shown at right by dragging and dropping the active top of its individual slidebar. The preferred slidebars are scaled from 0 to 100 for whatever set of parameters they control.

Within the Loudness Mapping category, a first adjustment that can be made is under the label "Audiophile Harmony" 174 to adjust noise management, which is a combined adjustment of both the noise reduction features and the low frequency compression features of the preferred DSP amplifiers in the hearing aid. In the most preferred DSP amplifiers, Layered Noise Reduction technology includes an algorithm which acts to remove noise between speech syllables, as well as lowering general background noise from the environment. Overall, the LNR function in the DSP amplifier 176 (shown in FIG. 21) can be set to the following settings: Off, Low (7 dB), Medium (10 dB), High (13 dB), and Max (17 dB). Separately, compression thresholds settings for each frequency channel in the DSP amplifier 176 can be set from 20 dB SPL to 82 dB SPL, in 2 dB steps. The Audiophile Harmony slide bar 174 allows selection of these settings, and preferably also controls related noise reduction parameters in the DSP amplifier 176, such as on and off status and biQuad coefficients for first and second noise filters in the DSP amplifier 176. Additionally, the Audiophile Harmony slide bar 174 may allow control over an input low cut filter which provides a 12 dB/octave smooth linear roll off below the corner frequency, with programmable corner frequency values of 250 Hz, 500 Hz, 750 Hz, 1 kHz, 1.25 kHz, 1.5 kHz, 2 kHz, 2.5 kHz, 3 kHz.

Within the Loudness Mapping category, a second adjustment that can be made is under the label "3D Reach Dynamic" 178, which primarily selects compression mode and adjusts attack and release compression time constants of the preferred DSP amplifier 176 in the hearing aid 166. In the most preferred DSP amplifiers, for each frequency channel of the amplifier 176, the compression modes (Basic, Fast or Reach Down) and time constant settings are available as follows:

| Driver Setting | Basic | | Fast | | Reach Down | |
| --- | --- | --- | --- | --- | --- | --- |
| | attack (msec) | release (msec) | attack (msec) | release (msec) | range (dB) | release (msec) |
| 0 | 3 | 120 | not active | | not active | |
| 1 | 3 | 300 | | | | |
| 2 | 3 | 800 | | | | |
| 3 | 50 | 300 | 3 | 50 | | |
| 4 | 100 | 800 | 3 | 100 | | |
| 5 | 100 | 2000 | 3 | 100 | | |
| 6 | 400 | 15,000 | 3 | 100 | 12 | 600 |
| 7 | 400 | 15,000 | 3 | 100 | 18 | 600 |
| 8 | 400 | 15,000 | 3 | 100 | 24 | 600 |

The 3D Reach Dynamic slidebar 178 allows simultaneous adjustment of the compression mode and the attack and release time constants for all the frequency channels. In the most preferred embodiment of the sound map 170, the 3D Reach Dynamic value is one of the two that are solely controllable using its slidebar 178, i.e., moving the cursor 172 on the sound map 170 does not adjust 3D Reach Dynamic.

A third slide bar 180 presented in the Loudness Mapping category is labeled "Active Dynamic Processing" and provides compression management, primarily adjusting compression ratios within each frequency band. In the most preferred DSP amplifier 176, compression ratio settings in each frequency channel are adjustable from 1:1 to 8:1, in 35 steps. The Active Dynamic Processing slidebar 180 allows similtaneous adjustment of compression ratios for all the frequency channels.

A fourth slide bar 182 presented in the Loudness Mapping category is labeled "Acoustic Map", which primarily adjusts the compression threshold knee in each frequency band. In the most preferred DSP amplifier 176, compression thresholds settings for each channel can be set from 20 dB SPL to 82 dB SPL, in 2 dB steps. The Acoustic Map slidebar 182 allows similtaneous adjustment of compression threshold knees for all the frequency bands.

Within the Cognitive Tonotopy category, a first adjustment that can be made is under the label "Barkbase Soundscape" 184, which primarily adjusts the frequency band specific gains, also referred to as band equalizer or BEQ values. The band gain adjusters are used to handle frequency shaping, with the most preferred DSP amplifier 176 providing each band with an adjustable gain in 2 dB steps from 0 dB to −40 dB. In general terms, the Barkbase soundscape slidebar 184 is a speech filter for reducing mid frequencies by pulling down on the slidebar 184 and raising mid-frequencies by lifting the slidebar 184 up, both in a stepped fashion. One setting on the Barkbase Soundscape slidebar 184 leaves BEQ values equally unadjusted. A first step or second step upward raises some or all of the BEQ values overall, such as raising all BEQ values below 4 kHz by +2 dB or +4 dB. A first step downward provides a curved adjustment to the BEQ values, from no adjustment in the highest frequency band(s), to a −8 dB adjustment in a middle frequency band around 1 kHz, to a −2 dB adjustment in the lowest frequency band.

A second adjustment in the Cognitive Tonotopy category is under the label "Brilliance". This slidebar 186 simultaneously adjusts the BEQ values covering the 1-3 kHz midrange frequencies, in steps of 2 dB, such as raising the midrange frequencies by +2 dB, +4 dB, or +6 dB. The 1-3 kHz midrange frequencies contain much of the sound information the brain needs to process and understand speech, so the Brilliance slidebar 186 can be thought of as a speech gain control.

A third adjustment in the Cognitive Tonotopy category is under the label "Perception". The Perception slidebar 188 simultaneously adjusts both the corner frequency of the input low cut filter, as well as the BEQ values covering the 3-8 kHz highrange frequencies.

A fourth adjustment in the Cognitive Tonotopy category is under the label "5 k High Res Audio". To understand this control 190, it is useful to think of frequency band pairs, particularly for higher frequency (over 4 kHz) bands. Raising the 5 k High Res Audio slidebar 190 brings the two BEQ values within the frequency band pairs closer together. For instance, consider a frequency band pair (say, 5 kHz and 5.5 kHz) where the lower frequency band (5 kHz) has an initial BEQ value of −6 dB and the upper frequency band (5.5 kHz) has an initial BEQ value of −10 dB. Raising the 5 k High Res Audio slidebar 190 one step would change the BEQ in the lower frequency band to −7 dB and simultaneously change the BEQ in the higher frequency band to −9 dB. Similar "averaging" type changes would be made in each of the high frequency band pairs. Raising the 5 k High Res Audio slidebar 190 another step would change the BEQ in the lower frequency band to −8 dB and simultaneously change the BEQ in the higher frequency band to −8 dB. Raising the 5 k High Res Audio slidebar 190 a third step would then make no further change the −8 dB values, but might have an effect in other frequency band pairs, until each BEQ value in the frequency band pair was the same as the other BEQ value in the frequency band pair.

Within the MPO category, a first adjustment that can be made is under the label "MPO" 190. The preferred amplifier 176 allows its maximum power output (MPO) to be limited using a compression limiter, which (unlike peak clipping) does not create harmonic distortion. In each compression channels, the MPO can be programmed to the settings of: Off or anywhere from 0 dB to −28 dB (relative to maximum output) in 2 dB steps. The output limiter threshold is not affected by the volume control setting, since the limiter is placed right before the output stage and after the volume control block. The MPO slidebar 192 allows simultaneous adjustment of all the MPO values in all compression channels. In the most preferred embodiment of the sound map 170, the MPO value is one of the two that are solely controllable using its slidebar 192, i.e., moving the cursor 172 on the sound map 170 does not adjust MPO.

A second adjustment within the MPO category is labeled "Speech Headroom". The Speech Headroom slidebar 194 sets the attack time of the MPO to allow more MPO for a limited time. More speech headroom is a slower MPO attack and a longer MPO release time, while less speech headroom has faster MPO attack time and faster MPO release time.

FIG. 8 shows two additional MICrophone slidebars, which are omitted from the embodiment of FIG. 20. One of these slidebars allows control over the Cocktail Party Effect setting on the microphone input. The other MICrophone slidebar allows control over the Pinna Effect setting on the microphone input.

The preferred sound map 170 shown at the left in FIG. 20 allows simultaneous control over eight of the ten slidebar variables, all based on the cognitive abilities of the patient. In general terms, the sound map 170 is separated into four quadrants, with icons 196, 198, 200, 202 displayed on the screen to indicate the appropriate situation for each quadrant. Moving the circular cursor 172 toward the top right generally causes the values of the "Audiophile harmonie", "perception" and "5 kRES Audio" to increase, whereas moving the circular cursor 172 toward the upper left generally causes the values of the "Acoustic map" to decrease, but causes the values of "Brilliance" and "Speech headroom" to generally increase. The settings toward the upper left quadrant tend to be appropriate for restaurant situations, and a restaurant icon 196 is positioned toward the upper left of the soundmap 170. The settings toward the upper right quadrant tend to be appropriate for party situations, and a party icon 198 is positioned toward the upper right of the soundmap 170. The settings toward the lower left quadrant tend to be appropriate for face to face conversational situations, and a conversation icon 200 is positioned toward the lower left of the soundmap 170. The settings toward the lower right quadrant tend to be appropriate for public address situations, and a public address icon 202 is positioned toward the lower right of the soundmap 170. Though not necessarily implemented in the software code this way, the concept of how the eight slidebar variables are controlled with a single sound map 170 is further explained relative to the example of the Active Dynamic Processing slidebar 180 explained conceptually in FIG. 21.

Next to each of these four icons 196, 198, 200, 202 and around the active area of the soundmap 170, there are four "ability meter" symbols 204. These "ability meter" symbols 204 summarize the expected ability of the patient in each of the four situations (restaurant, party, conversation and public address), based upon the cognitive loss score (points) and hearing comprehension setting (shape and color) as described previously with reference to FIGS. 1-7 and 9-19 (and assuming that the cognitive loss score (points) and hearing comprehension setting (shape and color) have been input into the fitting software application).

An important benefit of the preferred software application involves limiting the ranges of various variables which can be controlled based on the hearing or cognitive abilities of the patient. The user (most commonly the patient, but it could also be an audiologist or other staff person) is not permitted to make changes of hearing device parameters that are outside the range of benefit to that particular patient at that particular time, according to the current hearing and deprivation conditions of that particular patient. This is further explained with reference to FIG. 21 and additional examples outlined below.

Figure 21:
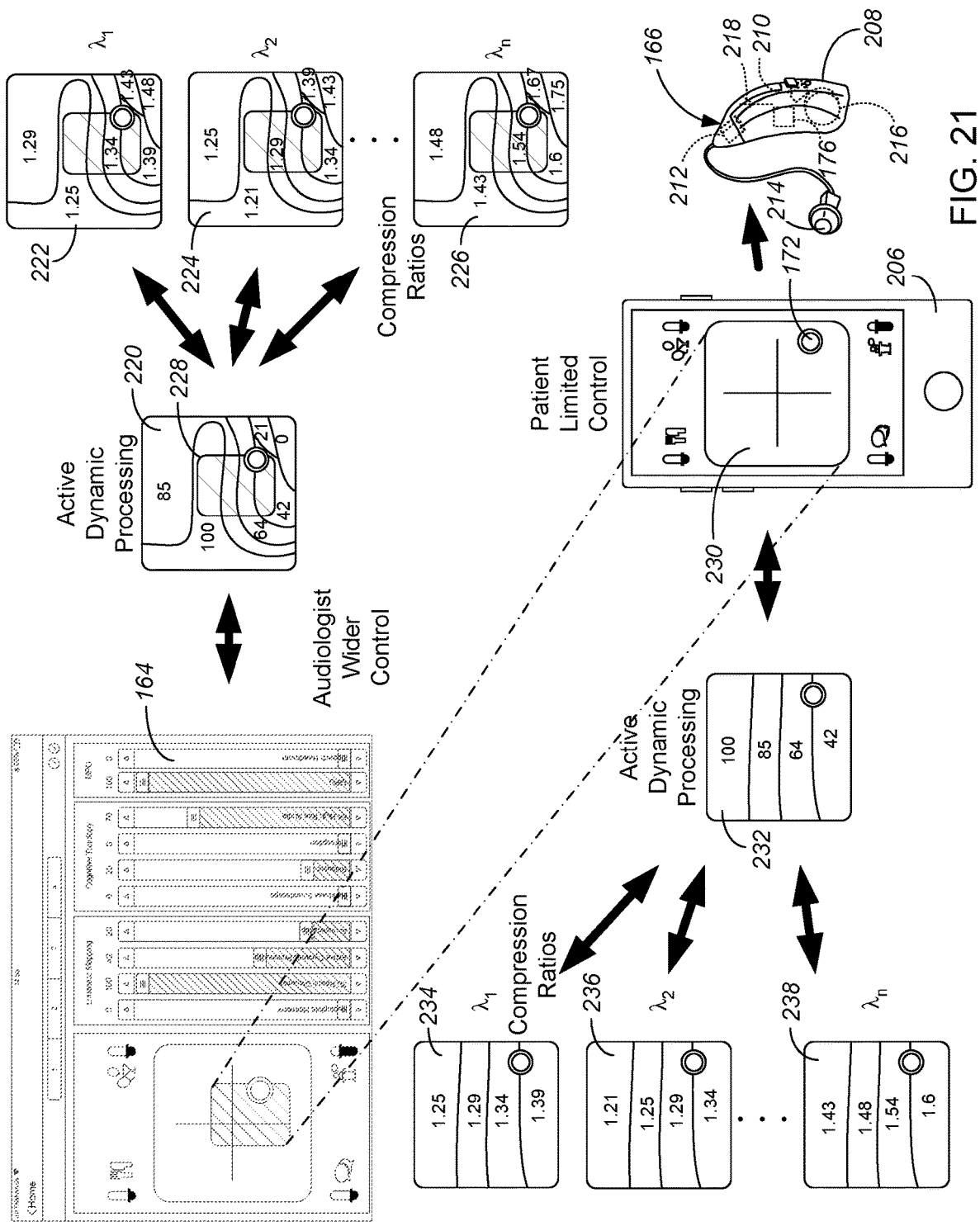
FIG. 21 is a screen shot comparison between the audiologist fitting software application and a fitting user interface running on a computing device of a hearing device user, such as on a smartphone.

FIG. 21 includes a patient's computing device 206 running a fitting software application in accordance with the present invention, and in wired or wireless communication with a hearing aid 166 or other hearing assist device. The hearing assist device 166, in this case depicted as a behind-the-ear hearing aid, has a housing 208 and includes a microphone 210, a digital signal processor ("DSP") 176 and a speaker (receiver) 212 with a sound outlet 214 directed into the patient's ear canal (not shown), powered by a replaceable or rechargeable battery 216, such as the hearing aids further disclosed in U.S. Pat. Nos. 7,519,193, 8,355, 517, 8,358,797 and 8,767,987, all assigned to the assignee of the present invention and each incorporated by reference. The hearing aid 166 also includes an antenna/chipset 218 for receiving a wireless signal, which can preferably include control data and/or audio data (such as from an audio streaming device, not shown), and/or may alternatively receive control data over a wired connection or directly programmed or burned into the DSP 176. While FIG. 21 depicts usage on an iPhone 206, the patient's fitting software application could alternatively be on the patient's iPad or other tablet, laptop computer or desktop computer. Both the audiologist's software application and the patient's software application are available for any type of computing device platform (Tablet, smartphone, PC, Mac). Further, the terms "audiologist's" and "patient's" are used herein merely for ease of understanding relative to the most common use case; these terms are not intended to indicate ownership of the device or the software license, nor even necessarily the identity of the person running the software application, but rather to demonstrate that at least one of the software applications (the "patient's" software application) can be limited in its range of control of DSP parameters relative to either the other software application or the full range of control of the respective DSP parameter in the hearing device 166. The patient's computing device 206 is in communication with the audiologist's computer, such as using wired or wireless transmissions or the communication scheme of U.S. patent application Ser. No. 16/600,703, incorporated by reference.

To take advantage of the "limited range" aspect of the present invention, it is important for the software to have an understanding of the cognitive abilities of the patient. In the preferred embodiment, this involves obtaining the patient's current cognitive loss score (points) and their current hearing comprehension setting (shape and color) as described previously with reference to FIGS. 1-7 and 9-19. In some embodiments, the data can be acquired simply because all the computer screens shown in FIGS. 2-7 and 9-19 are from the same computer in the same session as the computer providing the screens 52, 164 shown in FIGS. 8 and 20. In other embodiments, the patient's cognitive loss score (points) and comprehension setting (shape and color) are directly input into the fitting software application. In yet other embodiments, the patient's cognitive loss score (points) and comprehension setting (shape and color) are downloaded into one or both fitting software applications from the cloud server.

An important benefit of the preferred software application involves limiting the ranges of various variables which can be controlled based on the hearing or cognitive abilities of the patient. The user (patient) is not permitted to make changes of hearing device parameters that are outside the range of benefit to that particular patient at that particular time, according to the current hearing and deprivation conditions of that particular patient. For example, for a patient with low hearing cognition skills, the preferred fitting software running on the patient's smartphone 206 cannot make changes that could adversely affect and make the patient's hearing cognition worse. Thus, not only are the DSP parameters for the initial fitting selected by the software according to code (color and shape) and the overall point worth of deprivation + individual points as described above, but the ranges of permitted values allowed in the smartphone sound map 230 are limited relative to the ranges of values allowed in the audiologists soundmap 170. The goal in the software algorithm which selects the permissive ranges in the smartphone sound map 230 is to avoid any setting that would lead to discomfort and/or to too much brain work, to avoid too much effort by the patient as he/she retrains the cognitive abilities of his/her brain.

For instance, taking the example of the Active Dynamic Processing slidebar 180, for a patient having a given cognitive loss score (points) of 6350 (cognitive deprivation is minimal) and comprehension setting (shape and color) of green triangle (left ear) and green triangle (right ear), the fitting software algorithm determines six different slidebar values for "Active Dynamic Processing" which can be selected by the audiologist. When scaled on a 0 to 100 scale, these are 0, 21, 42, 64, 85 and 100. Each of these values correspond to different regions on the 2-D soundmap 170. If the user (audiologist) moves the circular cursor 172 to the far left side, at any elevation, the Active Dynamic Processing value is 100. Similarly, if the user (audiologist) has the cursor 172 at a middle elevation, and for the most part regardless of right-left position, the Active Dynamic Processing value is 100. However, as the user (audiologist) moves the cursor 172 to the lower right (toward the "public address" icon 202), the Active Dynamic Processing value will decrease through the available values to the lowest scaled value of 0. As the user (audiologist) moves the circular cursor 172 to the upper right (toward the "party" icon 198), the Active Dynamic Processing value will decrease but only to a scaled value of 85. Accordingly, for the Active Dynamic Processing variable for this particular patient at this particular time, the 2-D sound map 170 on the audiologist's fitting software can be viewed as mapping into six different regions shown in the concept drawing 220 in the upper middle of FIG. 2. This concept drawing 220 is never presented by the software, but merely conceptually translates what the user (audiologist) could determine by manipulating the circular cursor 172 to different areas of the soundmap 170 and watching the values output on the Active Dynamic Processing slidebar 180. In this example, the user (audiologist) has moved the circular cursor 172 into the area with the Active Dynamic Processing scaled value of 42, so this 42 value appears in the positioning and for Active Dynamic Processing slide bar 180.

As noted above, the Active Dynamic Processing scaled value simultaneous controls compression ratios for all the frequency channels, and FIG. 21 also shows conceptual mappings 222, 224, 226 for compression ratios in three such frequency bands. For the example of this particular patient at this particular time (green triangle, 6350 score), each scaled value on the Active Dynamic Processing map 220 correlates to a compression ratio value in each frequency channel. Thus, for instance, the Active Dynamic Processing scaled value of 100 (for this patient) might correlate to a compression ratio of 1.25 in the first lowest frequency band $\lambda_1$, to a compression ratio of 1.21 in the second lowest frequency band $\lambda_2$, etc. to a compression ratio of 1.43 in the highest frequency band $\lambda_n$. Because the user (audiologist) moved the circular cursor 172 to an area for Active Dynamic Processing with a scaled value of 42, the resultant setting of compression ratio in the first lowest frequency band $\lambda_1$ (i.e., the corresponding location of the circular cursor within map 222) would change to 1.39, the resultant setting of compression ratio in the second lowest frequency band $\lambda_2$ (i.e., the corresponding location of the circular cursor within map 224) would change to 1.34, etc., and the resultant setting of compression ratio in the highest frequency band $\lambda_n$ (i.e., the corresponding location of the circular cursor within map 226) would change to 1.6.

However, there are Active Dynamic Processing settings available on the audiologist's soundmap 170, and compression ratio settings achieveable in the DSP 176, which are of no use to this particular patient given his/her current cognitive abilities (6350, green triangle). The preferred audiologist's soundmap 170 presents a useful area 228, viewed by the audiologist in the fitting software application. This lets the audiologist know that moving the circular cursor 172 to a location outside the useful area 228 (or moving the slidebar 180 to select a scaled value for Active Dynamic Processing which does not occur within the useful area 228 of the concept map 220), is not appropriate for this patient at this time. For this example, when the useful area 228 is considered on the concept map 220, the only Active Dynamic Processing values within the useful area 228 are 100, 85, 64 and 42. By searching the useful area 228 using the cursor 172, the audiologist would be able to determine that moving the slidebar 180 to a scaled value of 0 or 21 would not be useful for the current cognitive skills of this particular patient.

For the fitting software application running on the patient's computing device (iPhone 206), the intent is to have the software limit the available ranges of finetuning of the DSP 176 in accordance with the patient's cognitive skills. Instead of having the identical soundmap to the soundmap 170 presented to the audiologist, the patient's soundmap 230 is limited to the useful area 228. This can be readily achieved just by scaling the useful area 228 in the x- and/or y-directions. FIG. 21 also shows a concept mapping 232 of the patient's soundmap 230, showing the Active Dynamic Processing scaled values within the soundmap 230 of 100, 85, 64 and 42. Accordingly, with the soundmap 230 presented to the patient being so scaled, it is always 100% safe for the patient to select any location on the patient's soundmap 230 for setting the parameters of the hearing aid 166.

For this particular patient at this particular time, the 2-D sound map 230 on the patient's fitting software can be viewed as a subset of the 2-D sound map 170 on the audiologist's fitting software corresponding to the useful area 228, i.e., mapping into only four different regions of scaled values of 100, 85, 64 and 42. This concept drawing 232 is again never presented by the software, but merely conceptually translates what the patient user could determine by manipulating the circular cursor 172 to different areas of the smartphone soundmap 230, transferring those values back into the audiologist's fitting software (such as using the transfer scheme of U.S. patent application Ser. No. 16/600,703, incorporated by reference), and checking which values were output on the Active Dynamic Processing slidebar 180. Conceptual map 232 is thus just the active area portion of conceptual map 220. Conceptual mappings 234, 236, 238 shown in FIG. 21 show the compression ratios in the same three frequency bands. Each conceptual mapping 234, 236, 238, showing the compression ratio settings achieveable in this example of the patient's soundmap 230, is the active area portion of its corresponding conceptual mapping 222, 224, 226.

Figure 22:
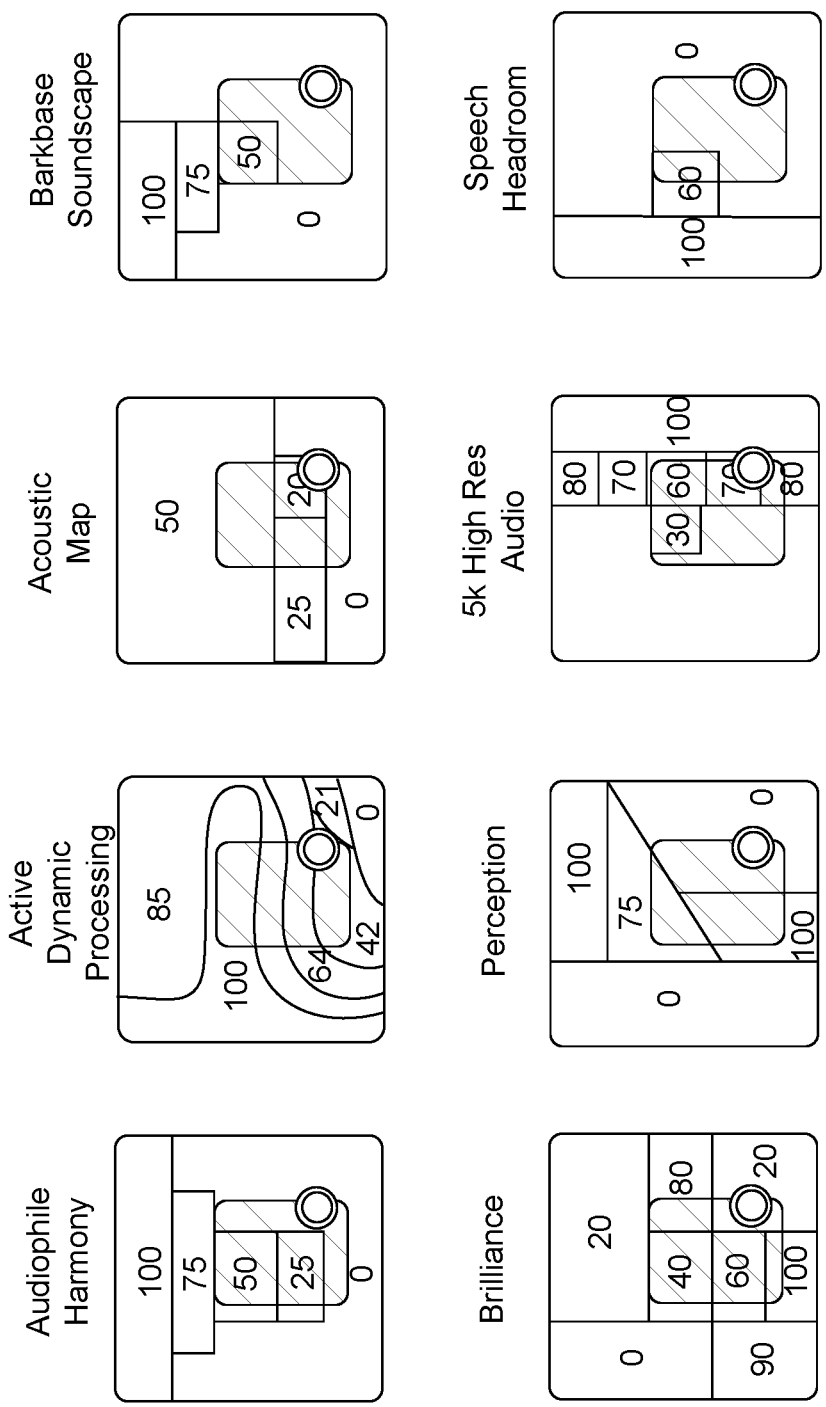
FIG. 22 is a presentation of concept mappings for eight variables preferably controlled by the soundmap of the audiologist fitting software application.

It should be understood that similar concept mappings can be developed for each of the eight variables controlled in the soundmaps 170, 230. FIG. 22 presents examples of such concept drawings for this particular patient (having a given cognitive loss score (points) of 6350 (cognitive deprivation is minimal) and comprehension setting (shape and color) of green triangle (left ear) and green triangle (right ear). In each case the soundmap 170 of the audiologist fitting software application allows more control over the eight variables, but also having a useful area 228 which is a subregion of the audiologist soundmap 170, with that useful area subregion scaled to the size of the patient's smartphone soundmap 230. The patient cannot use his or her smartphone soundmap 230 to select any value, for any of the eight variables which are controllable, to a value which is not 100% safe for the current cognitive ability (deprivation points) and hearing profile (shape, color) of the patient.

As conceptually explained above, the audiologist soundmap 170, the active area 228/patient's soundmap 230, and the variable ranges of the slidebars 174, 178, 180, 182, 184, 186, 188, 192, 194 are all selected by the preferred algorithms based on the current cognitive ability (deprivation points) and hearing profile (shape, color) of the patient. For further disclosure, considering the most preferred DSP amplifier 176 of an IntriCon AUDION 16 amplifier, two examples are as follows:

For the patient having a green triangle hearing loss in each ear, with a cognitive deprivation point score of 6350 (with a score of 6000 points or higher, cognitive deprivation is considered to be zero), the slidebar control, sound map 170 and useful area 228/sound map 230 translate into DSP control generally as follows:

A. Audiophile harmony: LNR is initially set to low (−7 dB), with the ability to raise to—max (−17 dB) or lower to off (0 dB)(i.e., the slidebar 174, sound map 170 and useful area 228/sound map 230 all permit the full range of layered noise reduction control allowed by the amplifier 176);

B. 3D Reach—is not controlled by either soundmap 170 or sound map 230, but is set in the fitting software to a scaled value of 100, resulting in an compression attack time constant of 3 msec and a compression release time constant of 120 msec. The slidebar 178 can be used to provide more comfort for the user by lowering the scaled value down from 100, which results in raising the compression attack and release time constants in accordance with the table presented previously;

C. Adaptive dynamic processing: For a midrange frequency band, the compression ratio is set to 1.21. The remaining fifteen frequency bands have their compression ratios selected for an appropriate curve of compression ratios relative to the 1.21 midrange compression ratio. The slidebar 180 and the full sound map 170 allow the midrange compression ratio to be adjusted up to five steps down to 1:43, with equal step changes applied to the other fifteen compression ratios. The size of the useful area 228/control allowed in the soundmap 230 relative to the slidebar 180 and sound map control depends on slidebar settings of other variables.

D. Acoustic map: For a midrange frequency band, the compression threshold is set to 44 dB SPL. The remaining fifteen frequency bands have their compression thresholds selected for an appropriate curve of compression thresholds relative to the 44 dB SPL midrange compression threshold. The slidebar 182 allow the midrange compression ratio to be increased from one to three steps up to 50 dB SPL or decreased from one to three steps down to 38 dB SPL, with equal step changes applied to the other fifteen compression ratios. For this particular patient, the audiologists' sound map 170 only allows decreases to the compression ratios. The size of the useful area 228/control provided in the patient's soundmap 230 depends on slidebar settings of other variables.

E. Barkbase soundscape: Initially sets the band EQ gains for all sixteen bands to −20 dB. The slidebar 184 and the soundmap 170 have a first step down, where the following adjustments are made: BEQ1 and BEQ7, −2 dB; BEQ2 and BEQ6, −4 dB; BEQ3 and BEQ5, −6 dB, BEQ4, −8 DB; BEQ8 through BEQ16, no change. The slidebar 184 allows up to three steps up, increasing BEQ1 through BEQ8 by +2, +4 or +6 dB, respectively, but making no change to BEQ 9 through BEQ16. The soundmap 170 only allows up to two steps up. The useful area 228 is sized such that the patient's soundmap 230 only allows a single step up or a single step down.

F. Brilliance: From the initial values (depends on the Barkbase soundscape scaled value as described above), the slidebar 186 and the soundmap 170 allows BEQ3 through BEQ6 to be moved one or two steps down, decreasing BEQ3 through BEQ6 by 2 or 4 dB respectively, or to be moved one, two or three steps up, increasing BEQ3 through BEQ6 by 2, 4 or 6 dB respectively. The size of the useful area 228 and control provided in the patient's soundmap 230 depends on other slidebar settings.

G. Perception: The slidebar 188 and both soundmaps 170, 230 allow the corner frequency of the input low cut filter to be unadjusted or increased one step. The slidebar 188 and soundmap 170 allows BEQ7 through BEQ16 to be increased up to one step upward, i.e., by 2 dB, or to be decreased up to two steps downward, i.e., by 2 or 4 dB.

H. 5 k High Res: The control provided by the slidebar 190 and both soundmaps 170, 230 depends on whether the audiologist has separately made adjustments to BEQ9 through BEQ16, in accordance with the "pair averaging" algorithm as described above.

I. MPO: Each of the sixteen MPOs is initially set to 0. Neither sound map 170, 230 has any effect. The slidebar 192 allows control of from one to fourteen steps, consistently changing each of the sixteen MPO values from −2 to −28 dB in 2 dB steps.

J. Speech Headroom: MPO attack time is initially unadjusted (DSP standard setting). The slidebar 194 and the audiologist soundmap 170 allows up to five step changes in accordance with the DSP permitted values. The patient soundmap 230 allows no change to MPO attack time.

Now we consider an example where the patient has having a light blue circle hearing loss in the left ear and a light blue square hearing loss in the right ear, with a cognitive deprivation point score of 3900 (cognitive deprivation is considered to be high). As compared to the first patient, the slidebar control, sound map 170 and useful area 228/soundmap 230 translate into DSP control as follows:

A. Audiophile harmony: LNR is initially set to high (−13 dB), with the ability to raise to −max (−17 dB) or lower to low (−70 dB)(i.e., the slidebar 174, sound map 170 and useful area 228/soundmap 230 are all limited to avoid high un-comfort sounds);

B. 3D Reach: no change relative to first patient example.

C. Adaptive dynamic processing: For a midrange frequency band, the compression ratio is initially set to 1.6. The slidebar 180 and sound map 170 only allow up to three steps down.

D. Acoustic map: No change relative to first patient example.

E. Barkbase soundscape: Slidebar 184 only allows up to two steps up, but otherwise as described above for the first patient example.

F. Brilliance: The slidebar 186 and the soundmap 170 only allow one step down and up to two steps up (relative to the five steps in total for the first patient example).

G. Perception: The slidebar 188 and soundmap 170 only allow BEQ7 through BEQ16 to be decreased by one step.

H. 5 k High Res: The "pair averaging" algorithm only allows three steps.

I. MPO: no change relative to first patient example.

J. Speech Headroom: no change relative to first patient example.

While the previous discussion discloses one preferred embodiment of the entire system, several aspects should be understood. Most importantly, the system algorithms and user interfaces are continually being analyzed and improved to provide better results for the cognitive abilities and hearing loss of the vast majority of patients. Both the algorithm for how to convert a hearing loss (color and shape) and cognitive score (deprivation points) into initial DSP settings, and the algorithm for how much adjustment will be allowed to each variable in the fitting finetuning software, are heavily dependent upon the particular DSP amplifier and its abilities and settings. For any DSP amplifier, the scaled value of 0 to 100 of a slidebar can translated into changes in the DSP settings. But other DSP amplifiers may allow control of other parameters, a higher or lower fidelity of control of any given parameter, etc. Even with the most preferred DSP amplifier, each exact algorithm which translates the 0 to 100 value of each of the slidebar settings into each collection of DSP settings is continually being reviewed and analyzed to see if it can be improved, thereby providing better results for more patients. Which slidebars are presented in the audiologist user interface, and which collections of DSP settings are being controlled by each slidebar, are similarly under continuous review for potential improvement. Each of the algorithms translating between the soundmap 170 and the 0 to 100 slidebar scaled values is similarly under continuous review, analysis and improvement. Accordingly, while the present application provides particular examples of DSP settings, audiologist soundmap 170, audiologist active area 228, patient soundmap 230, and conceptual mappings 220, 222, 224, 226, 232, 234, 236, 238 and those shown in FIG. 22, with one particular DSP amplifier 176 and for two particular patients, each of these will change and be improved over time as performance results for different patients are analyzed and reviewed.

Separately or in addition, while the description explains how the patient's smartphone fitting software can be limited relative to the audiologist's soundmap 170 and slidebar controls, it should be understood that identical or similar range limitations can be inserted earlier in the system. For instance, if unlicensed or inexperienced users will be performing the finetuning of the hearing aid 166, the range of adjustments permitted in the audiologist's soundmap 170 and/or in the audiologist's slidebars could be limited in the same way as described for the useful area 228 and the soundmap 230 controllable by the patient. Thus, although the present invention has been described with reference to preferred embodiments, workers skilled in the art will recognize that changes may be made in form and detail without departing from the spirit and scope of the invention.

The invention claimed is:

1. A method for fitting a hearing assist device for a patient, comprising:

conducting a test to assess aural cognitive abilities of the patient; and providing a user interface which allows adjustment of a plurality of sound processing parameter values within a digital signal processor in the hearing assist device, in which the range of sound processing parameter values permitted in the user interface is a limited subset of the values allowed within the digital signal processor, limited based on the assessed aural cognitive abilities.

2. The method of claim 1, in which the user interface comprises a control which allows limited adjustment of noise reduction features of the digital signal processor, limited based on the assessed aural cognitive abilities.

3. The method of claim 1, in which the user interface comprises a control which allows limited adjustment of attack and/or release compression time constants in the digital signal processor, limited based on the assessed aural cognitive abilities.

4. The method of claim 1, in which the user interface comprises at least one control which allows limited adjustment of one or more compression ratios in the digital signal processor, limited based on the assessed aural cognitive abilities.

5. The method of claim 4, in which a single control adjusts a plurality of compression ratios, but less than all the compression ratios in the digital signal processor.

6. The method of claim 1, in which the user interface comprises at least one control which allows limited adjustment of one or more compression threshold knees in the digital signal processor, limited based on the assessed aural cognitive abilities.

7. The method of claim 6, in which a single control adjusts a plurality of compression threshold knee settings, but less than all the compression threshold knee settings in the digital signal processor.

8. The method of claim 1, in which the user interface comprises at least one control which allows limited adjustment of one or more frequency band equalizer gain values in the digital signal processor, limited based on the assessed aural cognitive abilities.

9. The method of claim 8, in which a single control adjusts a plurality of frequency band equalizer gain values, but less than all the frequency band equalizer gain values in the digital signal processor.

10. The method of claim 1, in which the user interface comprises a single control which adjusts a plurality of maximum power outputs in frequency bands in the digital signal processor.

11. The method of claim 1, in which the user interface comprises a plurality of controls, each of which allows a limited adjustment of a set of parameters in the digital signal processor, limited based on the assessed aural cognitive abilities.

12. The method of claim 11, in which the user interface comprises a two dimensional sound map, the sound map allowing simultaneous adjustment of at least two of the plurality of controls.

13. A graphical user interface for fitting a hearing assist device for a particular patient, comprising:

a two dimensional sound map allowing simultaneous adjustment of at least two controls, each of the two controls allowing a limited adjustment of a set of parameters in a digital signal processor of the hearing assist device, wherein parameter values are limited based on an input value for assessed aural cognitive abilities of a patient.

14. The graphical user interface of claim 13, wherein the graphical user interface further comprises:

a first slidebar for adjusting multiple values within one set of parameters in the digital signal processor; and a second slidebar for adjusting multiple values within another set of parameters in the digital signal processor.

15. The graphical user interface of claim 14, further comprising:

a third slidebar for adjusting multiple values within a third set of parameters in the digital signal processor, in which the sound map does not control any values within the third set of parameters.

16. The graphical user interface of claim 14, wherein the first slidebar allows selection of at least some parameter values which are not possible using only the sound map.

17. A software system for fitting a hearing assist device for a particular patient, comprising:

an audiologist graphical user interface allowing simultaneous adjustment of a plurality of parameters in a digital signal processor of the hearing assist device, each parameter being settable to a parameter value within a range; and a patient graphical user interface allowing simultaneous adjustment of the plurality of parameters in the digital signal processor of the hearing assist device;

wherein the ranges of parameter values which are settable using the patient graphical user interface are limited relative to the ranges of parameter values which are settable using the audiologist graphical user interface.

18. The software system of claim 17, wherein the ranges of parameter values which are settable using the patient graphical user interface are limited based on an input value for assessed aural cognitive abilities of the patient.

19. The software system of claim 17, wherein the audiologist graphical user interface comprises a two dimensional sound map allowing simultaneous adjustment of a plurality of parameters in a digital signal processor of the hearing assist device; and wherein the patient graphical user interface comprises a two dimensional sound map allowing simultaneous adjustment of the plurality of parameters in the digital signal processor of the hearing assist device.

* * * * *